(12) United States Patent
Campbell et al.

(10) Patent No.: US 8,911,789 B2
(45) Date of Patent: *Dec. 16, 2014

(54) METHODS AND APPARATUS FOR MANUFACTURING PLASMA BASED PLASTICS AND BIOPLASTICS PRODUCED THEREFROM

(71) Applicants: Carnegie Mellon University, Pittsburgh, PA (US); Allegheny-Singer Research Institute, Pittsburgh, PA (US); Carmell Therapeutics Corporation, Pittsburgh, PA (US)

(72) Inventors: Phil G. Campbell, Cranberry Township, PA (US); James E. Burgess, Gibsonia, PA (US); Lee E. Weiss, Pittsburgh, PA (US); Jason Smith, Pittsburgh, PA (US)

(73) Assignees: Carnegie Mellon University, Pittsburgh, PA (US); Allegheny-Singer Research Institute, Pittsburgh, PA (US); Carmell Therapeutics Corporation, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/792,691

(22) Filed: Mar. 11, 2013

(65) Prior Publication Data

US 2013/0189370 A1    Jul. 25, 2013

Related U.S. Application Data

(63) Continuation of application No. 12/104,728, filed on Apr. 17, 2008, now Pat. No. 8,529,956, which is a continuation-in-part of application No. 11/873,751, filed on Oct. 17, 2007, now Pat. No. 8,293,530.

(60) Provisional application No. 60/852,368, filed on Oct. 17, 2006, provisional application No. 60/961,580, filed on Jul. 23, 2007.

(51) Int. Cl.
| | |
|---|---|
| *A61K 35/16* | (2006.01) |
| *A61K 38/19* | (2006.01) |
| *A61K 38/22* | (2006.01) |
| *A61L 27/36* | (2006.01) |
| *A61K 38/18* | (2006.01) |
| *A61K 38/37* | (2006.01) |

(52) U.S. Cl.
CPC .............. *A61K 35/16* (2013.01); *A61K 38/19* (2013.01); *A61K 38/22* (2013.01); *A61L 27/3616* (2013.01); *A61K 38/18* (2013.01); *A61L 27/365* (2013.01); *A61K 38/37* (2013.01)
USPC ....... 424/530; 424/93.7; 424/93.72; 424/422; 424/423; 424/489; 424/499; 424/520; 424/529; 435/2; 435/372; 514/13.5; 514/13.6; 514/15.3

(58) Field of Classification Search
None
See application file for complete search history.

(56) References Cited

U.S. PATENT DOCUMENTS

| | | |
|---|---|---|
| 1,786,488 A | 10/1930 | Homberg |
| 2,385,802 A | 10/1945 | Ferry |
| 2,385,803 A | 10/1945 | Cohn et al. |
| 2,457,804 A | 1/1949 | Bower |
| 2,492,458 A | 12/1949 | Bering, Jr. |
| 2,533,004 A | 12/1950 | Ferry et al. |
| 2,576,006 A | 11/1951 | Ferry et al. |
| 3,523,807 A | 8/1970 | Gerendas |
| 3,918,099 A | 11/1975 | Fuhr et al. |
| 4,067,119 A | 1/1978 | Overton |
| 4,188,373 A | 2/1980 | Krezanoski |
| 4,352,883 A | 10/1982 | Lim |
| 4,440,921 A | 4/1984 | Allcock et al. |
| 4,474,751 A | 10/1984 | Haslam et al. |
| 4,474,752 A | 10/1984 | Haslam et al. |
| 4,474,753 A | 10/1984 | Haslam et al. |
| 4,478,822 A | 10/1984 | Haslam et al. |
| 4,495,174 A | 1/1985 | Allcock et al. |
| 4,548,736 A | 10/1985 | Muller et al. |
| 4,606,337 A | 8/1986 | Zimmermann et al. |
| 4,820,626 A | 4/1989 | Williams et al. |
| 4,880,622 A | 11/1989 | Allcock et al. |
| 4,902,508 A | 2/1990 | Badylak et al. |
| 4,956,178 A | 9/1990 | Badylak et al. |
| 5,112,457 A | 5/1992 | Marchant |
| 5,126,529 A | 6/1992 | Weiss et al. |
| 5,176,996 A | 1/1993 | Hogan et al. |

(Continued)

FOREIGN PATENT DOCUMENTS

| | | |
|---|---|---|
| DE | 100 18 987 | 10/2001 |
| EP | 0 701 801 | 3/1996 |

(Continued)

OTHER PUBLICATIONS

Authorized Officer H. G. Kang. International Search Report and Written Opinion in International Application No. PCT/US2012/022534, mailed Jul. 31, 2012, 11 pages.

(Continued)

*Primary Examiner* — Allison Fox
*Assistant Examiner* — Susan E Fernandez
(74) *Attorney, Agent, or Firm* — Fish & Richardson P.C.

(57) ABSTRACT

Blood-derived plastic articles prepared from compositions including blood and, in some embodiments, at least one crosslinking agent and/or at least one biological response modifier, that can be useful for biological applications such as wound repair and tissue grafts; methods of making and using the same; methods for assessing the concentration of a biological response modifier in an article; and systems for preparing blood-derived plastic articles are provided.

53 Claims, 4 Drawing Sheets

(56) References Cited

U.S. PATENT DOCUMENTS

| | | |
|---|---|---|
| 5,204,055 A | 4/1993 | Sachs et al. |
| 5,208,036 A | 5/1993 | Eppstein et al. |
| 5,256,775 A | 10/1993 | Froehler |
| 5,264,564 A | 11/1993 | Matteucci |
| 5,281,422 A | 1/1994 | Badylak et al. |
| 5,286,573 A | 2/1994 | Prinz et al. |
| 5,293,772 A | 3/1994 | Carr, Jr. |
| 5,301,415 A | 4/1994 | Prinz et al. |
| 5,301,863 A | 4/1994 | Prinz et al. |
| 5,352,463 A | 10/1994 | Badylak et al. |
| 5,372,821 A | 12/1994 | Badylak et al. |
| 5,410,016 A | 4/1995 | Hubbell et al. |
| 5,445,833 A | 8/1995 | Badylak et al. |
| 5,460,831 A | 10/1995 | Kossovsky et al. |
| 5,476,777 A | 12/1995 | Holly et al. |
| 5,502,034 A | 3/1996 | Holly et al. |
| 5,510,077 A | 4/1996 | Dinh et al. |
| 5,518,680 A | 5/1996 | Cima et al. |
| 5,523,293 A | 6/1996 | Jane et al. |
| 5,527,692 A | 6/1996 | Holly et al. |
| 5,554,389 A | 9/1996 | Badylak et al. |
| 5,573,784 A | 11/1996 | Badylak et al. |
| 5,585,007 A | 12/1996 | Antanavich et al. |
| 5,630,842 A | 5/1997 | Brodniewicz |
| 5,645,860 A | 7/1997 | Knapp, Jr. et al. |
| 5,653,925 A | 8/1997 | Batchelder |
| 5,695,998 A | 12/1997 | Badylak et al. |
| 5,700,289 A | 12/1997 | Breitbart et al. |
| 5,709,854 A | 1/1998 | Griffith-Cima et al. |
| 5,711,969 A | 1/1998 | Patel et al. |
| 5,716,413 A | 2/1998 | Walter et al. |
| 5,738,824 A | 4/1998 | Pfeifer |
| 5,753,267 A | 5/1998 | Badylak et al. |
| 5,755,791 A | 5/1998 | Whitson et al. |
| 5,841,950 A | 11/1998 | Wang et al. |
| 5,851,229 A | 12/1998 | Lentz et al. |
| 5,855,583 A | 1/1999 | Wang et al. |
| 5,863,297 A | 1/1999 | Walter et al. |
| 5,878,193 A | 3/1999 | Wang et al. |
| 5,878,913 A | 3/1999 | Fisher et al. |
| 5,885,619 A | 3/1999 | Patel et al. |
| 5,906,828 A | 5/1999 | Cima et al. |
| 5,916,524 A | 6/1999 | Tisone |
| 5,944,754 A | 8/1999 | Vacanti |
| 5,955,110 A | 9/1999 | Patel et al. |
| 5,997,575 A | 12/1999 | Whitson et al. |
| 6,004,573 A | 12/1999 | Rathi et al. |
| 6,037,457 A | 3/2000 | Lord |
| 6,054,122 A | 4/2000 | MacPhee et al. |
| 6,074,663 A | 6/2000 | Delmotte et al. |
| 6,083,902 A | 7/2000 | Cederhom-Williams |
| 6,099,567 A | 8/2000 | Badylak et al. |
| 6,102,850 A | 8/2000 | Wang et al. |
| 6,124,265 A | 9/2000 | Timmons et al. |
| 6,139,574 A | 10/2000 | Vacanti et al. |
| 6,143,203 A | 11/2000 | Zeng et al. |
| 6,143,293 A | 11/2000 | Weiss et al. |
| 6,165,486 A | 12/2000 | Marra et al. |
| 6,187,039 B1 | 2/2001 | Hiles et al. |
| 6,203,573 B1 | 3/2001 | Walter et al. |
| 6,217,894 B1 | 4/2001 | Sawhney et al. |
| 6,233,504 B1 | 5/2001 | Das et al. |
| 6,241,981 B1 | 6/2001 | Cobb et al. |
| 6,270,793 B1 | 8/2001 | Van Dyke et al. |
| 6,274,341 B1 | 8/2001 | Baily et al. |
| 6,287,813 B1 | 9/2001 | Fussenegger et al. |
| 6,302,898 B1 | 10/2001 | Edwards et al. |
| 6,306,177 B1 | 10/2001 | Felt et al. |
| 6,319,715 B1 | 11/2001 | Luo et al. |
| 6,322,785 B1 | 11/2001 | Landesberg et al. |
| 6,325,808 B1 | 12/2001 | Bernard et al. |
| 6,331,181 B1 | 12/2001 | Tierney et al. |
| 6,331,319 B1 | 12/2001 | Badylak et al. |
| 6,331,578 B1 | 12/2001 | Turner et al. |
| 6,331,579 B1 | 12/2001 | Sanborn |
| 6,375,989 B1 | 4/2002 | Badylak et al. |
| 6,379,710 B1 | 4/2002 | Badylak |
| 6,385,509 B2 | 5/2002 | Das et al. |
| 6,394,998 B1 | 5/2002 | Wallace et al. |
| 6,395,029 B1 | 5/2002 | Levy |
| 6,399,144 B2 | 6/2002 | Dinh et al. |
| 6,454,811 B1 | 9/2002 | Sherwood et al. |
| 6,472,162 B1 | 10/2002 | Coelho et al. |
| 6,485,723 B1 | 11/2002 | Badylak et al. |
| 6,485,751 B1 | 11/2002 | Wang |
| 6,530,958 B1 | 3/2003 | Cima et al. |
| 6,547,994 B1 | 4/2003 | Monkhouse et al. |
| 6,548,729 B1 | 4/2003 | Seelich et al. |
| 6,589,557 B2 | 7/2003 | Straub et al. |
| 6,653,291 B1 | 11/2003 | Badylak et al. |
| 6,692,738 B2 | 2/2004 | Maclaughlin et al. |
| 6,705,850 B1 | 3/2004 | Fofonoff |
| 6,730,299 B1 | 5/2004 | Tayot et al. |
| 6,740,736 B2 | 5/2004 | McCreath |
| 6,808,659 B2 | 10/2004 | Schulman et al. |
| 6,855,329 B1 | 2/2005 | Shakesheff et al. |
| 6,921,412 B1 | 7/2005 | Black et al. |
| 6,979,307 B2 | 12/2005 | Beretta et al. |
| 6,998,418 B1 | 2/2006 | Sung et al. |
| 7,056,722 B1 | 6/2006 | Coelho et al. |
| 7,135,027 B2 | 11/2006 | Delmotte |
| 7,148,209 B2 | 12/2006 | Hoemarm et al. |
| 8,017,157 B2 | 9/2011 | Yoo et al. |
| 8,293,530 B2 | 10/2012 | Burgess et al. |
| 8,529,956 B2 | 9/2013 | Campbell et al. |
| 8,529,958 B2 | 9/2013 | Campbell et al. |
| 8,529,959 B2 | 9/2013 | Campbell et al. |
| 8,529,960 B2 | 9/2013 | Campbell et al. |
| 8,529,961 B2 | 9/2013 | Campbell et al. |
| 2001/0005488 A1 | 6/2001 | Hirao et al. |
| 2001/0051833 A1 | 12/2001 | Walter et al. |
| 2002/0022861 A1 | 2/2002 | Jacobs et al. |
| 2002/0054901 A1 | 5/2002 | Gainey et al. |
| 2003/0054330 A1 | 3/2003 | Fischer et al. |
| 2003/0175410 A1 | 9/2003 | Campbell et al. |
| 2004/0078077 A1 | 4/2004 | Binette et al. |
| 2004/0124564 A1 | 7/2004 | Noorjahan et al. |
| 2004/0146543 A1 | 7/2004 | Shimp et al. |
| 2005/0042210 A1 | 2/2005 | Akai |
| 2005/0142208 A1 | 6/2005 | Yoo et al. |
| 2005/0158535 A1 | 7/2005 | Zhang et al. |
| 2005/0226904 A1 | 10/2005 | Choi et al. |
| 2006/0019389 A1 | 1/2006 | Yayon et al. |
| 2006/0093644 A1 | 5/2006 | Quelle et al. |
| 2006/0172008 A1 | 8/2006 | Yayon et al. |
| 2006/0241776 A1 | 10/2006 | Brown et al. |
| 2007/0036766 A1 | 2/2007 | Kevy et al. |
| 2007/0037737 A1 | 2/2007 | Hoemann et al. |
| 2007/0148142 A1 | 6/2007 | Yoo et al. |
| 2007/0191761 A1 | 8/2007 | Boone et al. |
| 2008/0003272 A1 | 1/2008 | Rapp et al. |
| 2008/0286329 A1 | 11/2008 | Campbell et al. |
| 2010/0254900 A1 | 10/2010 | Campbell et al. |
| 2012/0003193 A1 | 1/2012 | Campbell et al. |
| 2012/0003279 A1 | 1/2012 | Campbell et al. |
| 2012/0003324 A1 | 1/2012 | Campbell et al. |
| 2012/0177694 A1 | 7/2012 | Campbell et al. |
| 2012/0191027 A1 | 7/2012 | Campbell et al. |

FOREIGN PATENT DOCUMENTS

| | | |
|---|---|---|
| EP | 1 275 397 | 1/2003 |
| FR | 2 583 334 | 12/1986 |
| JP | 08117323 | 5/1996 |
| RU | 2067448 | 10/1996 |
| VU | WO 95/24929 | 9/1995 |
| WO | WO 81/00516 | 3/1981 |
| WO | WO 86/03122 | 6/1986 |
| WO | WO 95/11007 | 4/1995 |
| WO | WO 95/15763 | 6/1995 |
| WO | WO 96/20698 | 7/1996 |
| WO | WO 96/22115 | 7/1996 |
| WO | WO 97/47254 | 12/1997 |
| WO | WO 98/12274 | 3/1998 |

(56) References Cited

FOREIGN PATENT DOCUMENTS

| WO | WO 98/14135 | 4/1998 |
|---|---|---|
| WO | WO 01/78968 | 10/2001 |
| WO | WO 03/007873 | 1/2003 |
| WO | WO 03/079985 | 10/2003 |
| WO | WO 03/084937 | 10/2003 |
| WO | WO 03/094937 | 11/2003 |
| WO | WO 2005/037108 | 4/2005 |
| WO | WO 2007/126411 | 11/2007 |
| WO | WO 2007/127834 | 11/2007 |
| WO | WO 2009/014776 | 1/2009 |

OTHER PUBLICATIONS

Aeschlimann et al., "Cross-linking of laminin-nidogen complexes by tissue transglutaminase. A novel mechanism for basement membrane stabilization," *J Biol Chem*, 1991, 266:15308-17.

Aeschlimann et al., "Tissue transglutaminase and factor XIII in cartilage and bone remodeling," *Semin Throm Hemost*, 1996, 22:437-43.

Aeschlimann et al., "Transglutaminases: protein cross-linking enzymes in tissues and body fluids," *Throm Haemost*, 1994, 71:402-15.

Amon et al., "Improving manufacturing quality by combining experimental and statistical methods," Proceedings of the 1997 NSF Design and Manufacturing Grantees Conference, Society of Manufacturing Engineers, 1997. Seattle, W A.

Amon et al., "Shape deposition manufacturing with microcasting: processing, thermal and mechanical issues," *ASME Journal of Manufacturing Science and Engineering*, 1998, 120:656-667.

Amrani et al., "Wound healing. Role of commercial fibrin sealants," *Ann N Y Acad Sci*, 2001, 936:566-79.

Angerer et al., "Regulative development of the sea urchin embryo: signaling cascades and morphogen gradients," *Semin Cell Dev Biol*, 1999, 10:327-34.

Arras et al., "The delivery of angiogenic factors to the heart by microsphere therapy," *Nat Biotechnol*, 1998, 16:159-62.

Aspenberg et al., "Dose-dependent stimulation of bone induction by basic fibroblast growth factor in rats," *Acta Orthop. Scand.*, 1991, 62:481-484.

ASTM Method No. 4508-06, 2007, pp. 528-533.

ASTM Method No. 6272-02, 2007, pp. 519-526.

ASTM Method No. D256-06a, 2007, pp. 1-20.

ASTM Method No. D5045-99, 2007, pp. 795-803.

ASTM Method No. D-638-03, 2007, pp. 50-63.

ASTM Method No. D695-02a, 2007, pp. 78-85.

ASTM Method No. D790-07, 2007, pp. 1-11.

Baffour et al., "Enhanced angiogenesis and growth of collaterals by in vivo administration of recombinant basic fibroblast growth factor in a rabbit model of acute lower limb ischemia: Dose-dependent effect of basic fibroblast growth factor," *J. Vasco Surg.*, 1992, 16:181-191.

Bailey et al., "Chemical, Clinical, and Immunological Studies on the Products of Human Plasma Fractionation. XXII, Fibrin Films in Neurosurgery, with Special Reference to Their Use in the Repair of Dural Defects and in the Prevention of Meningocerebral Adhesions," *J. Clin. Invest.*, 1944, 23(4):597-600.

Bale et al., "Strain enhancement of elastic modulus in fine fibrin clots," *Throm Res*, 1988, 52:565-72.

Basilico et al., "The FGF family of growth factors and oncogenes," *Advance Cancer Res.*, 1992, 59:115-165.

Bates et al., "Vascular endothelial growth factor and microvascular permeability," 6:83-96 *Microcir.*, 1999, 6:83-96.

Baustista et al., "Insulin-like growth factors I and II are present in the skeletal tissue often vertebrates," *Metabolism*, 1993, 39:96-100.

Bauters et al., "Recovery of disturbed endothelium-dependent flow in the collateral-perfused rabbit ischemic hindlimb following administration of vascular endothelial growth factor," *Circulation*, 1995, 91:2802-2809.

Bedino, "Embalming Chemistry: Glutaraldehyde Versus Formaldehyde," *Expanding Encyclopedia of Mortuary Practices*, 2003, 649:2614-2632.

Bellamkonda et al., "Review: Tissue Engineering in the Nervous System," *Biotechnology and Bioengineering*, 1994, 43:543-544.

Bosch et al., "Guided bone regeneration in calvarial bone defects using polytetrafluorethylene membranes," *Cleft Palate Craniofac J*, 1995, 32:311-7.

Bose et al., "Processing of bioceramic implants via fused deposition process," in Solid Freeform Fabrication Symposium. 1998 Austin, TX, 8 pages.

Bousfield et al., "Nonlinear analysis of the surface tension driven breakup of viscoelastic filaments," *J. Non-Newtonian Fluid Mech.*, 1986, 21:79-97.

Brittland et al., "Micropatterning Proteins and Synthetic Peptides on Solid Supports: A Novel Application for Microelectronics Fabrication Technology," *Biotechnology Progress*, 1992, 8:155-160.

Brown et al., "Fibroblast migration in fibrin gel matrices," *Am J Pathol*, 1993, 142:273-83.

Burgess et al., "Characterization and cDNA Cloning of phospholipase C-$\gamma$, a major substrate for heparin-binding growth factor I (acidic fibro blast growth facto) -activated tyrosine kinase," *Mol. Cell. Biol.*, 1990, 10:4770-4777.

Burgess et al., "The heparin-binding (fibroblast) growth factor family of proteins," *Ann. Rev. Biochem.*, 1989, 58:575-606.

Butler et al. "Secretion of Recombinant Human Fibrinogen by the Murine Mammary Gland," *Transgenic Res.*, 2004, 13:437-450.

Butler et al., "Current Progress in the Production of Recombinant Human Fibrinogen in the Milk of Transgenic Animals," *Thromb. Haemost.*, 1997, 78:537-542.

Campbell et al., "Autologous Plastics", Poster presentation (Mar. 3, 2007), 1 page.

Campbell et al., "Autologous Plastics", Slide Presentation (Feb. 12, 2007), 9 pages.

Campbell et al., "Biomaterial modification of bone growth enhancement: Covalent bonding of insulin-like growth factor-1 to metal surfaces," 81st Endocrine Society Meeting. 1999, 1 page.

Campbell et al., "Insulin-like growth factor (IGF)-bindingprotein-5-(201-218) region regulates hydroxyapatite and IGF-I binding," *Am J. Physiol.*, 1997, 273:E1005-13.

Campbell et al., "Insulin-like growth factor binding protein (IGFBP) inhibits binding and biological activity of IGFs on human osteosarcoma cells.," *J Cell Physiol*, 1991, 149:293-300.

Campbell et al., "Insulin-like growth factor-binding protein-3 binds fibrinogen and fibrin," *J. Biol. Chem.*, 1999, 274:30215-21.

Carmeliet, "Mechanisms of angiogenesis and arteriogenesis," *Nature Med*, 2000, 6:389-95.

Carr et al., "Effect of fibrin structure on plasmin-mediated dissolution of plasma clots," *Blood Coagul Fibrinolysis*, 1995, 6:567-73.

Chen et al., "$\gamma$-$\gamma$ cross-linking sites in human and bovine fibrin," *Biochemistry*, 1971, 10:4487-91.

Chen et al., "Gradient micro pattern immobilization of EGF to investigate the effect of artificial juxtacrine stimulation," *Biomaterials*, 2001, 22:2453-7.

Christani et al., "Surface tension driven jet break up of strain-hardening polymer solutions," *Journal of Non-Newtonian Fluid Mechanics*, 2001, 100:9-26.

Chu et al. "Ceramic SFF by Direct and indirect stereolithography," in Materials Research Society Fall Meeting. 119-123,1999. Boston, MA.

Ciano et al., "Macrophage migration in fibrin gel matrices," *Lab Invest*, 1996, 54:62-70.

Cima et al., Computer-derived microstructures by 3D Printing: Bio- and Structural Materials. Solid Freeform Fabrication Symposium. 1994. The University of Texas at Austin, 10 pages.

Clark, "Fibrin and wound healing," *Ann N Y Acad Sci*, 2001, 936:355-67.

Clark, "Fibrin sealant in wound repair: a systematic survey of literature," *Expert Opin Investig Drugs*, 2000, 9:2371-92.

Cohn, "The Separation of Blood into Fractions of Therapeutic Value," *Annals of Internal Med.*, 1947, 26(3):341-352.

Cooper et al., "Automated Fabrication of Complex Molded Parts Using Mold SDM," *Materials and Design*, 1999, 20:83-89.

Cornejo et al., "Development of Bioceramic Tissue Scaffolds via FDC," *Ceramic Transaction*, 2000, 110:183-195.

(56) References Cited

OTHER PUBLICATIONS

Crawford et al., "Solid Freeform Fabrication: A New Manufacturing Paradigm," *IEEE Spectrum*, 1999, 36:34-43.
Cronkite et al., "Use of Thrombin and Fibrinogen in Skin Grafting," *JAMA*, 1994, 124:976-8.
Curling, "Integrating New Technology into Blood Plasma Fractionation," *Bio Pharm*, 2002, 6 pages.
Dallas, "Measuring interactions between ECM and TGF beta-like proteins," *Methods Mol. Biol.*, 2000, 139:231-43.
de Man et al., "Antigenic Properties of Bioplast," *Int. J. Oral Surg.*, 1978, 7:564-568.
Definition of particulate from www.definition.com, pp. 1-4. Accessed Sep. 18, 2008, 4 pages.
Djabourov et al., "Structure and Rheology of Gelatin and Collagen Gels," *Biorheology*, 1993, 30:191-205.
Doi et al., Derwent Acc No. 1996-281087, English abstract only of JP 08117323 about. 1997.
Draghi et al., "Microsphere leaching for scaffold porosity control," *Journal of Materials Science: Materials in Medicine*, 2005, 16:1093-1097.
Drew et al., "Wound-healing defects in mice lacking fibrinogen," *Blood*, 2001, 97:3691-8.
Dubey et al., "Neuronal contact guidance in magnetically aligned fibrin gels: effect of variation in gel mechano-structural properties," *Biomaterials*, 2001, 22:1065-75.
Dunstan et al., "Systemic administration of acidic fibroblast growth factor (FGF-1) prevents bone loss and increases new bone formation in ovariectomized rats," *J Bone Min. Res.*, 1999, 14:953-959.
Dutta et al., "Layered Manufacturing: Current Status and Future Trends," *Trans. ASME JCISE*, 2001, 1:60-71.
Eiselt et al., (1998) Development of technologies aiding large-tissue engineering, Biotechnol Prog, 14:134-40.
Elcin et al., "Extensive in vivo angiogenesis following controlled release of human vascular endothelial cell growth factor: implications for tissue engineering and wound healing," Artif Organs, 2001, 25:558-65.
Elisseeff et al., "Controlled-release of IGF-I and TGF-beta 1 in a photopolymerizing hydrogel for cartilage tissue engineering," *J Orthop Res*, 2001, 19:1098-1104.
Entchev et al., "Gradient formation of the TGF-beta homolog Dpp," *Cell*, 2000, 103:981-91.
Eppley et al., "Angiogenic enhancement in bone graft healing by basic fibroblast growth factor," *Clin. Res.*, 1988, 36:A851.
Eppley et al., "Enhancement of angiogenesis by bFGF in mandibular bone graft healing in the rabbit," *J. Oral Maxillofac. Surg.*, 1998, 46:391-398.
Eppley et al., "Platelet-Rich Plasma: A Review of Biology and Applications in Plastic Surgery," *Plast. Reconstr. Surg.*, 2006, 118(6):147e-15e, American Society of Plastic Surgeons.
Evans et al., "Current Applications of Fibrin Sealant in Urologic Surgery," *Int. braz. J. Urol.*, 2006, 14 pages printed from www.scielo.br.
Fasching et al., "Planning Robotic Trajectories for Thermal Spray Shape Deposition," *ASM Journal of Thermal Spray Technology*, 1993, 2:45-50.
Ferrara et al., "The biology of vascular endothelial growth factor," *Endocrine Reviews*, 1997, 18:4-25.
Ferry et al. "Preparation and Properties of Serum and Plasma Proteins. IX. Human Fibrin in the Form of an Elastic Film," *Am. Chem Soc. J.*, 1947, 69:400-409.
Ferry et al., "Chemical, Clinical, and Immunological Studies on the Products of Human Plasma Fractionation. XVI. Fibrin Clots, Fibrin Films and Fibrinogen Plastics," *Clin. Invest.*, 1944, 23:566-572.
Ferry et al., "Preparation and properties of serum and plasma protiens. VIII. The conversion of human fibrinogen to fibrin under various condictions," *J. of American Chem Society*, 1947, 69:388-400.
Fesus et al., "Transglutaminase-sensitive glutamine residues of human plasma fibronection revealed by studying its proteolytic fragments," *Eur J Biochem*, 1986, 154:371-4.

Filiz et al. "Micromilling of microbarbs for medical implants," *International Journal of Machine Tools & Manufacture*, 2008, 48:459-472.
Finkelman et al., "Quantitation of growth factors IGF-I, SGF/IGF-II/ and TGF-beta in human dentin," *J. Bone Miner. Res.*, 1990, 5:717-23.
Finlayson et al., "Crosslinking of rabbit fibrin in vivo," *Thromb Diath Haemorrh*, 1974, 31:435-8.
Folkman et al., "Angiogenesis research: guidelines for translation to clinical application," *Thromb Haemost*, 2001, 86:23-33.
Folkman, "Angiogenesis and angiogenesis inhibition: an overview," *Exs*, 1997, 79:1-8.
Folkman, "Angiogenesis—retrospect and outlook," *Exs*, 1992, 61:4-13.
Folkman, "How the field of controlled-release technology began, and its central role in the development of angiogenesis research," *Biomaterials*, 1990, 11:615-8.
Folkman, "Tumor angiogenesis," *Advances in Cancer Research*, 1974, 19:331-358.
Gelman et al., "Rigidity of fibring gels as measured by quasielastic light scattering," *Biopolymers*, 1980, 19:1259-70.
Gerendas, "Fibrin products as aids in hemostasis and wound healing," Fibrinogen, 1968, Laki, K., Ed., Marcel Dekker, New York, Chapter 13, pp. 277-316.
Gerendas, M. "Bioplasts and Their Use in Surgery," *Ther. Hung.*, 1959, 7:8-16.
Gilbert et al., "Production and Characterization of ECM Powder: Implications for Tissue Engineering Applications," *Biomaterials*, 2005, 26:1431-5.
Giordano et al., "Mechanical properties of dense polylactic acid structures fabricated by three dimensional printing," *J Biomater Sci Polym Ed*, 1996, 8:63-75.
Gladner et al., "Effects of crosslinking on the rigidity and proteolytic susceptibility of human fibrin clots," *Throm Res*, 1983, 30:273-88.
Goldin et al., "Breakup of laminar capillary jet of viscoelastic fluid," *J. Fluid Mech.*, 1969, 38:689-711.
Gorman et al., "Structural features of glutamine substrates for human plasma factor XIIIa (activated blood coagulation factor XIII)," *J Biol Chem*, 1980, 255:419-27.
Gorman et al., "Structural features of glutamine substrates for transglutaminases. Specificities of human plasma factor XIIIa and the guinea pig liver enzyme toward synthetic pepiides," *J Biol Chem.*, 1981, 256:2712-5.
Gorman et al., "Transglutaminase amine substrates for photochemical labeling and cleavable cross-linking of proteins," *J Biol Chem*, 1980, 255:1175-80.
Greenberg et al., "Transglutaminases: multifunctional crosslinking enzymes that stabilize tissues," *Faseb J*, 1991, 5:3071-7.
Griffith et al., "In vitro organogensis of liver tissue," *Ann N Y Acad Sci*, 1997, 831:382-97.
Gross et al., "The extended active site of guinea pig liver transglutaminase," *J Biol Chem*, 1975, 250:4648-55.
Gurdon et al., "Single cells can sense their position in a morphogen gradient," *Development*, 1999, 126:5309-17.
Gutowska et al., "Injectable gels for tissue engineering," *Anat Rec*, 2001, 263:342-9.
Hall et al., "Molecular properties of fibrin-based matrices for promotion of angiogensis in vitro," *Microvasc Res*, 2001, 62:315-26.
Hallman et al., "A clinical histologic study of bovine hydroxyapatite in combination with autogenous bone and fibrin glue for maxillary sinus floor augmentation Results after 6 to 8 months of healing," *Clin Oral Implants Res*, 2001, 12:135-143.
Hauschka et al., "Growth factor effects in bone," in *the Osteoblast and Osteocyte*. B.K. Hall (Eds.), The Telfor Press, Inc., 1990, 103-170.
Hayen et al., "Hyaluronan stimulates tumor cell migration by modulating the fibrin fiber architecture," *J Cell Sci*, 1999, 112 (Pt 13):2241-51.
Herbert et al., "Effects of fibrin micromorphology on neurite growth from dorsal root ganglia cultured in three-dimensional fibrin gels," *J Biomed Mater Res*, 1998, 40:551-9.
Herbert et al., "Effects of fibrinolysis on neurite growth from dorsal root ganglia cultured in two- and three-dimensional fibrin gels," *J Comp Neurol*, 1996, 365:380-91.

(56) References Cited

OTHER PUBLICATIONS

Hettasch et al., "Analysis of factor XIII substrate specificity using recombinant human factor XIII and tissue transglutaminase chimeras," *J Biol Chem*, 1997, 272:25149-56.
Hollinger et al., "Poly(alpha-hydroxy acid) carrier for delivering recombinant human bone morphogenetic protein-2for bone regeneration," *J. Controlled Release*, 1996, 39:287-304.
Hollinger et al., "Recombinant human bone morphogenetic protein-2 and collagen for bone regeneration," *J. Biomed. Mater. Res.*, 1998, 43(4):356-364.
Hollister et al., (1998) "Design and Manufacture of HA Biomaterial Scaffold for Bone Tissue Engineering," in Trans. 44th Orthopaedic Research Society, 1 page.
Hu et al., "Angiogenin promotes invasiveness of cultured endothelial cells by stimulation of cell-associated proteolytic activities," *Proc Natl Acad Sci USA*, 1994, 91:12096-100.
Huber et al., "Consequences of seven novel mutations on the expression and structure of keratinocyte transglutaminase," *J Biol Chem*, 1997, 272:21018-26.
Isner et al., "Clinical evidence of angiogenesis after arterial gene transfer of ph VEGF165 in patient with ischemic limb," *The Lancet*, 1996, 348:370-375.
Isner, J. "The role of angiogenic cytokines in cardiovascular disease," *Clin. Immunol. Immunopathol.*, 1996, 80:S82-S91.
Jackson et al., "Fibrin sealant: current and potential clinical applications," *Blood Coag. Fibrinolysis*, 1996, 7:737-746.
Kachurin et al. "Direct-Write Construction of Living Tissue," in Mat. Res. Symp. 2002: Materials Research Society, 698:351-356.
Kaihara et al., "Silicon micromachining to tissue engineer branched vascular channels for liver fabrication," *Tissue Eng*, 2000, 6:105-17.
Katstra et al., "Oral dosage forms fabricated by three dimensional printing," *J Control Release*, 2000, 66:1-9.
Kiernan, "Formaldehyde, Formalin, Paraformaldehyde and Glutaraldehyde: What they are and What They Do," *Microscopy Today*, 2000, 00-1, pp. 8-12.
Kim et al., "Survival and function of hepatocytes on a novel three-dimensional synthetic biodegradable polymer scaffold with an intrinsic network of channels," Ann. Surg, 1998, 228:8-13.
King et al., "Development and in vitro characterization of vascular endothelial growth factor (VEGF)-loaded poly(DL-lactic-co-glycolic acid)/poly(ethylene glycol) microspheres using a solid encapsulation/single emulsion/solvent extraction technique," *J. Biomed Mater Res.*, 1999, 51:383-90.
Klasgsbrun et al., "Regulators of angiogenesis," *Annual Review Physiology*, 1991, 53:217-239.
Krewson et al., "Stabilization of nerve growth factor in controlled release polymers and in tissue," *J Biomater Sci Polym Ed*, 1996, 8:103-17.
Lasa et al., "Delivery of demineralized bone powder by fibrin sealant," *J. Plast. Reconstr. Surg.*, 1995, 96:1409-1417.
Laurencin et al., "Poly(lactic acid) and poly(glycolic acid): Orthopedic surgery applications, in Bone Formation and Repair," *American Academy of Orthopaedic Surgeons*, 1994, p. 325-340.
Laurencin et al., "Poly(lactide-co-glycolide)/hydroxyapatite delivery of BMP-2-producing cells: a regional gene therapy approach to bone regeneration," *Biomaterials*, 2001, 22:1271-7.
Laurencin et al., "Use of polyphosphazenes for skeletal tissue regeneration," *J. Biomats. Res.*, 1993, 27:963-973.
Leblanc et al., "Kinetic studies of guinea pig liver transglutaminase reveal a general-base-catalyzed deacylation mechanism," *Biochemistry*, 2001, 40:8335-42.
Lee et al., "Crosslinking of wild-type and mutant alpha 2-antiplasmins to fibrin by activated factor XIII and by a tissue transglutaminase," *J Biol Chem*, 2000, 275:37382-9.
Lee et al., "Degradable and injectable poly(aldehyde guluronate) hydrogels for bone tissue engineering," *J Biomed Mater Res*, 2001, 56:228-33.
Lee et al., "Healing of large segmental defects in rat femurs is aided by rhBMP-2 in PLGA matrix," *J. Biomed. Mater. Res.*, 1994, 28:1149-1156.
Lee et al., "Selective Laser Sintering of Bioceramic materials of Implants," Solid Freeform abrication Symposium, 1993, University of Texas at Austin, 5 pages.
Lee et al., "Tissue-engineered growth of bone by marrow cell transplantation using porous calcium metaphosphate matrices," *J Biomed Mater Res*, 2001, 54:216-23.
Leong et al., "Fabrication of porous polymeric matrix drug delivery devices using the selective laser sintering technique," *Proc Inst Mech Eng [H]*, 2001, 215:191-201.
Leung et al., "Vascular endothelial growth factor is secreted angiogenic mitogen," *Science*, 1989, 246:1306-1309.
Linkhart et al., "Growth factors for bone growth and repair: IGF, TGFβ, and BMP," *Bone*, 1996, 19:1-12.
Liu, "A Novel Use of Genipin-Fixed Gelatin as Extracellular Matrix for Peripheral Nerve Regeneration," *J. of Bio. App.*, 2004, 19(1):21-34.
Lockhart et al. "Expression monitoring by hybridization to high-density oligonucleotide arrays," *Nature Biotechnology*, 1996, 14:1675-1680.
Lom et al. "A Versatile Technique for Patterning Biomolecules Onto Glass Coverslips," *J. Neurosci. Methods*, 1993, 50:385-397.
Lorand et al., "Activation of the fibrin stabilizing factor of plasma by thrombin," *Arch. Biochem. Biophys.*, 1964, 105:58-67.
Lorand, "Factor XIII: structure, activation, and interactions with fibrinogen and fibrin," *Ann NY Acad Sci*, 2001, 936:291-311.
Lu et al., "TGF-beta I release from biodegradable polymer microparticles: its effects on marrow stromal osteoblast function," *J Bone Join Surg Am*, 2001, 83-A Suppl 1 :S82-S91.
Maes et al., "Impaired angiogenesis and endochondral bone formation in mice lacking the vascular endothelial growth factor isoforms VEGF(1 64) and VEGF(188)," *Mech Dev*, 2002, 111:61-73.
Marx, "RE. Platelet-rich plasma (PRP): What is PRP and what is not PRP?" *Implant Dentistry*, 2001, 10(4): 225-228.
Meinel et al., "Stabilizing insulin-like growth factor-I in poly(D,L-lactide-co-glycolide) micropsheres," *J. Control Release*, 2001, 70:193-202.
Micanovic et al., "Role of histidine 373 is the catalytic activity of coagulation factor XIII," *J Biol Chem*, 1994, 269:9190-4.
Mikos et al., "Laminated three dimensional biodegradable foams for use in tissue engineering," *Biomaterials*1993, 14:323-330.
Mitkevich et al., "Coagulation factor XIIIa undergoes a conformational change evoked by glutamine substrate. Studies on kinetics of inhibition and binding of XIIIa by a cross-reacting antifibrinogen antibody," *J Biol Chem*, 1998, 273:14387-91.
Monteiro et al., "Butterfly eyespot patterns: evidence for specification by a morphogen diffusion gradient," *Acta Biotheor*, 2001, 49:77-88.
Mooney et al., "Growing new organs," *Sci. Am.*, 1999, 280:60-65.
Mosesson et al., "The structure and biological features of fibrinogen and fibrin," *Ann NY Acad Sci*, 2001,936:11-30.
Mosesson, "The assembly and structure of the fibrin clot," *Nouv Ref Fr Hematol*, 1992, 34:11-6.
Mosher et al., "Cross-linking of fibronectin to collagen by blood coagulation Factor XIIIa," *J Clin Invest*, 1979, 64:781-7.
Muller et al., "Electron microscopy of fine fibrin clots and fine and coarse fibrin films. Observations of fibers in cross-section and in deformed states," *J Mol Biol*, 1984, 174:369-84.
Muller et al., "Rheological Characterization of the Gel Point—a New Interpretation," *Macromolecules*, 1991, 24:1321-1326.
Nakamura et al., "Stimulation of bone formation by intraosseous application of recombinant basic fibroblast growth factor in normal and ovariectomized rabbits," *J. Bone Joint Surg.*, 1997, 15:307-313.
Nam et al., "A Novel Fabrication Method of Macroporous Biodegradable Polymer Scaffolds Using Gas Foaming Salt as a Porogen Addi," *J of Biomed Materials Res.*, 2000, 10 pages.
Nehls et al., "A novel, microcarrier-based in vitro assay for rapid and reliable quantification of three-dimensional cell migration and angiogenesis," *Microvac Res.*, 1995, 50:311-22.
Nehls et al., "The configuration of fibrin clots determines capillary morphogenesis and endothelial cell migration," *Microvasc Res*, 1996, 51:347-64.
Neufeld et al., "Vascular endothelial growth factor (VEGF) and its receptors," *Faseb J.*, 1999, 13:9-22.

(56) References Cited

OTHER PUBLICATIONS

Newman et al., "Viscosity and elasticity during collagen assembly in vitro: Relevance to matrix-driven translocation," *Biopolymers*, 1997, 41:337-347.

Nowotny et al., "Preparation of fibrin clot samples for tensile stress-strain experiments," Biomaterials, 1981, 2:55-6.

Oklu et al., "The latent trans forming growth factor beta binding protein (LTBP) family [in Process Citation]," *Biochem. J.*, 2000, 352 Pt 3:601-10.

Ong et al., "Residual Stress Control Issues for Thermal Deposition of Polymers in SFF Processes," Solid Freeform Fabrication Proceedings. 2000, 209-218.

Onizawa (1987) [Purification and characterization of bone proliferation factors from bovine bone matrix], Kokubyo Gakkai Zasshi, 53:349-64.

Ono et al., "Bone-fibrin in spinal surgery," *Clinical Orthopaedics and Related Research*, 1992, 275:133-139.

Pedersen et al. "Mechanical Properties of the Skin: A Comparison Between Two Suction Cup Methods," *Skin Research and Technology*, 2003, 9:111-115, Blackwell Munksgaard, Denmark.

Pimbley et al., "Satellite Droplet Formation in a Liquid Jet," *IBM J. Res. Dev.*, 1977, 21:21-30.

Piper et al., "High selectivity of human tissue transglutaminase for immunoactive gliadin peptides: implications for celiac sprue," *Biochemistry*, 2002, 41:386-93.

Pitts et al., "Submicron Multiphoton Free-form Fabrication of Proteins and Polymers: Studies of Reaction Efficiencies and Applications in Sustained Release," *Macromolecules*, 2000, 33:1514-1523.

Podos et al., "Morphogen gradients: new insights from DPP," *Trends Genet*, 1999, 15:396-402.

Prince et al., "Osteopontin, a substrate for transglutaminase and factor XIII activity," *Biochem Biophys Res Commun*, 1991, 177:1205-10.

Prinz et al., "Novel Applications and Implementations of Shape Deposition Manufacturing," Office Naval Research, 1998, 19-26.

Prunkard et al. "High-Level Expression of Recombinant Human Fibrinogen in the Milk of Transgenic Mice," *Nat. Biotechnol.*, 1996, 4:867-871.

Radomsky et al., "Potential role of fibroblast growth factor in enhancement of fracture healing," *Clin. Orthop. Rel. Res.*, 1998, 355:283-293.

Ranieri et al. "Spatial Control of Neuronal Cell Attachment and Differentiation on Covalently Patterned Laminin Oligopeptide Substrates," *Intl. J Devel. Neurosci.*, 1994, 12(8):725-735.

Ribatti et al. "The Chick Embryo Chorioallantoic Membrane as an in vivo Wound Healing Model," *Pathol Res Pract*, 1996, 192:1068-1076.

Ribatti et al., "Chorioallantoic membrane capillary bed: a useful target for studying angiogenesis and anti-angiogenesis in vivo," *Anat Rec*, 2001, 264:317-24.

Ribatti et al., "The Chick Embryo Chorioallantoic Membrane as a Model for in vivo Research on Angiogenesis," *Int. J. Dev. Biol.*, 1996, 40(6):1189-1197.

Ribatti et al., "The chick embryo chorioallantoic membrane as a model for in vivo research on anti-angiogenesis," *Curr Pharm. Biotechnol*, 2000, 1:73-82.

Richardson et al., "Polymeric system for dual growth factor delivery," *Nat Biotechnol.*, 2001, 19:1029-34.

Ringeisen et al. "Cell-by-Cell Construction of Living Tissue," in Mat. Res. Symp. 2002:Materials Research Society.

Roberts et al., "Factors affecting the migration and growth of endothelial cells from microvessels of bovine retina," *Exp Eye Res*, 1990, 50:165-72.

Robinson et al., "Catalytic life of activated factor XIII in thrombi. Implications for fibrinolytic resistance and thrombus aging," *Circulation*, 2000, 102:1151-7.

Rodan et al., (1992) "Fibroblast growth factor and platelet derived growth factor," in Cytokines and Bone and Metabolism. M. Gowan (Eds.), CRC Press, p. 116-140.

Rodan et al., "Effects of acidic and basic fibroblast growth factors on osteoblastic cells," *Connect. Tissue Res.*, 1989, 20:283-238.

Rodan et al., "Growth stimulation of rat calvaria osteoblastic cells by acidic fibroblast growth factor," *Endocrinol.*, 1987, 121:1917-1923.

Rosengart et al., "Therapeutic angiogenesis: A comparative study of angiogenic potential of acidic fibroblast growth factor and heparin," *J. Vasc Surg*, 1997, 26:302-312.

Rowe et al., "Multimechanism oral dosage forms fabricated by three dimensional printing," *J Control Release*, 2000, 66:11-7.

Saharinen et al., "Latent transforming growth factor-beta binding proteins (LTBPs)—structural extracellular matrix proteins for targeting TGF-beta action," *Cytokine Growth Factor Rev.*, 1999, 10:99-117.

Sahni et al., "Potentiation of endothelial cell proliferation by fibrin(ogen)-bound fibroblast growth factor-2," *J Biol Chem*, 1999, 274:14936-41.

Sahni, A, Odrljin, T., and Francis, C.W. (1998) Binding of basic fibroblast growth factor fibrinogen and fibrin, J Biol Chem, 273:7554-9.

Sakai et al., (2001) Tissue transglutaminase facilitates the polymerization of insulin-like growth factor-binding protein-I (IGFBP-I) and leads to loss of IGFBP-I 's ability to inhibit insulin-like growth factor-I-stimulated protein synthesis, J Biol Chem, 276:8740-5.

Sakata et al., (1980) Cross-linking of alpha 2-plasmin inhibitor to fibrin by fibrin-stabilizing factor, J Clin Invest, 65:290-7.

Sakiyama et al., (1999) Incorporation of heparin-binding peptides in fibrin gels enhances neurite extension: an example of designer matrices in tissue engineering, Faseb J, 13:2214-24.

Sakiyama-Elbert et al.,(2000) Controlled release of nerve growth factor from a heparin-containing fibrin-based cell ingrowth matrix, J Control Release, 69:149-68.

Saltzman et al., (1999) Intracranial delivery of recombinant nerve growth factor: release kinetics and protein distribution for three delivery systems, Pharm Res, 16:232-40.

Sane et al., (1988) Vitronectin is a substrate for transglutaminases, Biochem Biophys Res Commun, 157:115-20.

Schense et al., (1999) Cross-linking exogenous bifunctional peptides in fibrin gels with factor XIIIa, Bioconjug Chem, 10:75-81.

Schlag et al., (1988) Fibrin sealant in orthopeadic surgery, Clin. Orthop. Rel. Res., 227:269-285.

Schmaltz et al., "Investigation of Transport Phenomena in Microeasting Shape Deposition ManuJacturing via Experiments Designed using Optimal Sampling," ASME National Heat Transfer Conference. 1997. Baltimore, Maryland.

Schmitz et al., (1986) The critical size defect as an experimental model for craniomandibulofacial nonunions, Clin. Orthop. Rel. Res., 205:299-308.

Schmitz et al., (1990) Characterization of a rat calvarial nonunion defects, Acta. Anat. Anatomica, 138:185-192.

Schonherr et al.,(2000) Extracellular matrix and cytokines: a functional unit [In Process Citation), Dev. Immunol, 7:89-101.

Schott et al., (1993) Growth factors and angiogenesis, Cardiovasc Res, 27:1155-61.

Schrier et al., (1999) Recombinant human bone morphogenetic protein-2 binding and incorporation in PLGA microsphere delivery systems, Pharm Dev Technol, 4:611-21.

Schwartz et al., (1989) The influence of fibrin sealant on demineralized bone marix-dependent osteoinduction, Clin Orthop Rel Res, 238:282-287.

Scott (2001) An assessment of reasonable tortuosity values, Pharm Res, 18:1797-800.

Shainoff et al., (1991) Immunoelectrophoretic characterizations of the cross-linking of fibrinogen and fibrin by factor XIIIa and tissue transglutaminase. Identification of a rapid mode of hybrid alpha/gamma-chain cross-linking that is promoted by the gamma-chain cross-linking, U. Biol. Chem., 266:6429-37.

Shen et al., (1975) Effects of calcium ion and covalent crosslinking on formation and elasticity of fibrin cells, Thromb Res, 6:255:65.

Shen et al., (1983) Contribution of fibrin stabilization to clot strength. Supplementation of factor XIII-deficient plasma with the purified zymogen, J Clin Invest, 71:1336-41.

Sierra et al., (1992) A method to determine shear adhesive strength of fibrin sealants, J Appl Biomater, 3:147-51.

(56) References Cited

OTHER PUBLICATIONS

Singhvi et al. (1994) Engineering Cell Shape and Function, Science, 264:696-698.
Singhvi et al., Review: Effect of Substratum Morphology on Cell Physiology, Biotechnology and Bioengineering, 1994, 43:764-771.
Sipe et al. (2004) Localization of Bone Morphogenetic Proteins (BMPs}-2, -4, and -6 within Megakaryocytes and Platelets, Bone, 35(6):1316-22, Elsvier, Inc.
Smith et al. (1995) Osseous regeneration in preclinical models using bioabsorbable delivery technology for recombinant human bone morphogenetic protein-2 (rhBMP-2), J. Controlled Rel., 36:183-195.
Soker et al., (2000) Systems for therapeutic angiogenesis in tissue engineering, World J Urol, 18:10-8.
Sorensen et al., (1994) Localization of trans glutaminase-reactive glutamine residues in bovine osteopontin, Biochem J, 304 (Ptl):13-6.
Springer et al., (1998) VEGF gene delivery to muscle: potential role for vasculogenesis in adults, Mol Cell, 2:549-58.
Strigini et al., (1999) Formation of morphogen gradients in the *Drosophila* wing, Semin Cell Dev Biol, 10:335-44.
Tabata et al., "De novo formation of adipose tissue by controlled release of basic fibroblast growth factor," *Tissue Eng*, 2000, 6:279-89.
Tabata, "Genetics of morphogen gradients," *Nat Rev Genet*, 2001, 2:620-30.
Takagi et al., "The reaction of the dura to bone morphogenetic protein (BMP) in repair of skull defects," *Ann Surg.*, 1982, 196:100-9.
Takeshita et al., "Gene transfer of naked DNA encoding for 3 isoforms of vascular endothelial growth factor stimulates collateral circulation development in vivo," *Lab. Invest.*, 1996, 75:487-502.
Takeshita et al., "In vivo evidence that vascular endothelial growth factor stimulates collateral formation by inducing arterial cell proliferation in a rabbit ischemic hindlimb," *J Am. Coli. Cardiol.*, 1994, 23:294A.
Takeshita et al., "Intramuscular administration of vascular endothelial growth factor induces dose-dependent collateral artery augmentation in a rabbit model of chronic limb ischemia," *Circulation*, 1994, 90:228-234.
Takeshita et al., "Microangiographic assessment of collateral vessel formation following direct gene transfer of vascular endothelial growth factor in rats," *Cardiovasc. Res.*, 1997, 35:547-552.
Takeshita et al., "Therapeutic angiogenesis: A single intra-arterial bolus of vascular endothelial growth factor augments collateral vessel formation in a rabbit ischemic hindlimb model," *J. Clin. Invest.*, 1994, 93:662-670.
Teleman et al., "Dpp gradient formation in the *Drosophila* wing imaginal disc," *Cell*, 2000, 103:971-80.
Toma et al., "Autologous fibrin glue in the repair of dural defects in craniofacial resections," *J Laryngol Otol*, 1992, 106:356-7.
Valentini et al., "Patterned Neuronal Attachment and Outgrowth on Suiface Modified, Electrically Charged Fluoropolymer Substrates," *J. Biomaterials Science Polymer Edition*, 1933, 5(1/2): 13 -36.
Van Hinsbergh et al., "Role of fibrin matrix in angiogenesis," *Ann NY Acad Sci*, 2001, 936:426-37.
Wang "Basic fibroblast growth factor for stimulation of bone formation in osteoinductive or conductive implants," *Acta. Orthop. Scand. Suppl.*, 1996, 269:1-33.
Wang et al., "Basic fibroblast growth factor enhances bone-graft incorporation: Dose and time dependence in rats," *J. Orthop. Res.*, 1996, 34:316-323.
Wang et al., "Basic fibroblast growth factor infused at different times during bone graft incorporation. Titanium chamber study in rats," *Acta. Orthop. Scand.*, 1996, 67:229-236.
Wang et al., "Basic fibroblast growth factor promotes ingrowth in porous hydroxyapatite," *Clin. Orthop. Rel. Res.*, 1996, 333:252-260.
Wang et al., "Characterization of matrix-induced osteogenesis in rat calvarial bone defects: II. Origins of bone-forming cells," *Calcif Tissue Int*, 1999, 65:486-93.
Weiss et al., "A Rapid Tool Manufacturing System Based on Stereolithography and Thermal Spraying," *ASME Manufacturing Review*, 1990.
Weiss et al., "Shape Deposition Manufacturing of Heterogeneous Structure," *SME Journal of Manufacturing Systems*, 1997, 16:239-248.
Weiss, "Process Overview Analytical Chapters," in NSF sponsored JTEC/WTEC panel report on rapid prototyping in Europe and Japan, International Technology Research Institute at Loyla College, 1997, p. 5-20.
Weiss, "Tissue Engineering: Solid Freeform Fabrication of Scaffolds," *Science & Medicine*, 2002, 8:6-7.
Wilting et al., "Effects of vascular endothelial growth factor and basic fibroblast growth factor: application with corneal grafts on the chorioallantoic membrane," *Acta Anal (Basel)*, 1993, 147:207-15.
Winter et al., "Analysis of Linear Viscoelasticity of a Cross-Linking Polymer at the Gel Point," *Journal of Rheology*, 1986, 30:367-382.
Wolpert, "Positional information and the spatial pattern of cellular differentiation," *Journal of Theoretical Biology*, 1969, 25:1-47.
Wong et al. "Fibrin-based Biomaterials to Deliver Human Growth Factors," *Thromb. Haemost*, 2003, 89:573-582.
Wu et al., "Acidic and basic FGFs dilate arterioles of skeletal muscle through NO-dependent mechanism," *Am. J. Physiol.*, 1996, 3:1087-1093.
Yancopoulos et al., "Vascular-specific growth factors and blood vessel formation," *Nature*, 2000, 407:242-248.
Yao et al., "Biocompatibilty and biodegradation of a bone composite containing tricalcium phosphate and genipin crosslinked gelatin," *Journal of Biomedical Material Research*, 2004, 69A:709-717.
Yao et al., "Preparation of networks of gelatin and genipin as degradable biomaterials," *Materials Chemistry and Physics*, 2004, 83:204-208.
Yarin, "Free Liquid Jets and Films: Hydrodynamics and Rheology," *Longman Sci. & Tech* 1993, 149 pages.
Ye et al., "Fibrin gel as a three dimensional matrix in cardiovascular tissue engineering," *Eur J. Cardiothorac Surg.*, 2000, 17:587-91.
Zein et al., "Processing of 3D scaffolds by fused deposition modeling," In International Workshop on Advances in Materials Science and Technology, 2000, Singapore.
Zinner et al., "A New Method of Arthroplasty," *Acta Med. Acad. Sci. Hung.*, 1954, 7:217-222.
Zisch et al., "Covalently conjugated VEGF-fibrin matrices for endothelialization," *J. Control. Release*, 2001, 72:101-113.
International Preliminary Report on Patentability in International Application No. PCT/US2012/022534, issued Jul. 30, 2013, 7 pages.
McNeill et al., "Intestinal vasoconstriction after hemorrhage: roles of vasopressin and angiotensin," Am. J. Physiol., 1970, 219(5):1342-1347.

METHODS AND APPARATUS FOR MANUFACTURING PLASMA BASED PLASTICS AND BIOPLASTICS PRODUCED THEREFROM

CROSS REFERENCE TO RELATED APPLICATIONS

This application is a continuation of U.S. patent application Ser. No. 12/104,728, filed Apr. 17, 2008, which is a continuation-in-part of U.S. patent application Ser. No. 11/873,751, filed Oct. 17, 2007, which claims the benefit of U.S. Provisional Patent Application Ser. Nos. 60/852,368, filed Oct. 17, 2006, and 60/961,580, filed Jul. 23, 2007, all of which are hereby incorporated by reference in their entireties.

FIELD OF THE INVENTION

The invention pertains to bioplastics for patient implantation or application, made at least in part from patient tissue or fluids such as plasma.

BACKGROUND OF THE INVENTION

Fibrin-based plastics were invented in the 1940s as part of a U.S. Defense-sponsored research program to develop medical strategies for wounded military personnel. For example, fibrin-based plastics were developed out of the human blood program led by Edwin Cohn at Harvard University. John Ferry, then at Woods Hole, led the group that was involved in developing fibrin elastomers. As a result of this work, elastomeric sheet forms of fibrin were developed and used successfully in neurosurgical applications, burn treatments, and peripheral nerve regeneration. See, for example, Ferry, J. D. et al., Clin. Invest. 23:566-572 (1944); Bailey, O. T. et al, J. Clin. Invest. 23:597-600 (1944); Cronkite et al., JAMA, 124: 976-8 (1944); and Ferry J. D. et al., Am. Chem. Soc J. 69:400-409 (1947). Hard fibrin plastics were fabricated into implants and were finding clinical success as early as the 1940s. See, for example, U.S. Pat. Nos. 1,786,488, 2,385,802, 2,385,803, 2,492,458, 2,533,004, 2,576,006, 3,523,807, 4,548,736 and 6,074,663, all incorporated herein by reference. Research sponsored by the Hungarian government led to the development of similar products in the 1950s through the early 1970s. Forms of hard plastic fibrin were demonstrated to have clinical efficacy in orthopedic applications of bone resurfacing. See, for example, Zinner, N. et al., Acta Med. Acad. Sci. Hung. 7:217-222 (1955); Gerendas, M., Ther. Hung., 7:8-16 (1959); and Gerendas, M., Chapter 13 in Fibrinogen, Laki, K., Ed., Marcel Dekker, New York, pp. 277-316 (1968).

Despite the efficacy of fibrin products, concerns about disease transmission from purified human fibrinogen from pooled plasma remained. However, during the late 1970s and thereafter, fibrin was developed as a tissue glue and sealant, and although this application required purified human fibrinogen, new techniques had been developed to ensure the safety of blood products. Consequently, fibrin-based glues and sealants have been used in clinical practice for over twenty years in Europe (and since 1998 in the United States) with no disease transmission concerns. Recently, the development of recombinant human fibrinogen and thrombin and purified salmon fibrinogen and thrombin have helped further to address concerns over both safety and market availability. See, for example, Butler S. P. et al., Transgenic Res. 13:437-450 (2004); Prunkard D. et al., Nat. Biotechnol. 4:867-871 (1996); Butler S. P. et al, "Thromb Haemost. 78:537-542 (1997); U.S. Pat. No. 5,527,692; U.S. Pat. No. 5,502,034; U.S. Pat. No. 5,476,777; U.S. Pat. No. 6,037,457; U.S. Pat. No. 6,083,902; and U.S. Pat. No. 6,740,736. Autologous sealants and glues are also available (see for example U.S. Pat. No. 6,979,307).

Despite such advances in the field, interest in the use of protein bioplastics in plastic forms, such as fibrin elastomers, has significantly declined over time. Silicone rubber sheets, which were introduced in the 1960s and 1970s, have supplanted fibrin elastomeric sheets in the clinic, despite inherent problems with their permanence. There are also limitations with current synthetic bioresorbable plastics, such as polyurethane, polylactic acid (PLA), polylactic-co-glycolic acid (PLGA), polyglycolic acid (PGA) and polycaprolactone. These polymers degrade in the body by hydrolysis, via bulk degradation, or through surface erosion, all of which operate independently of the surrounding biological environment. The inability of these polymers to degrade in response to cellular invasion and to promote directly the in-growth of host tissues remains a profound limitation of these types of bioresorbable implants.

In contrast, protein bioplastics can degrade in response to cellular proteolytic processes so that degradation occurs in concert with the growth and healing of host tissues.

Also, many synthetic materials do not inherently bind growth factors of interest for therapeutic delivery options, whereas fibrin binds to many growth factors directly and indirectly through molecular interactions with growth factors, including those with heparin binding domains. However, fibrin materials—including certain of the present inventors' own fibrin-based plastics based on purified fibrinogen/thrombin from pooled human or animal plasma—have certain constraints or limitations, such as not inherently containing endogenous growth factors. Moreover, fibrin materials of the prior art are very expensive, especially when prepared from human sources and with the required large amounts of starting material necessary to give desired yields. Commonly used synthetic materials, such as bioresorbable polymers, can be associated with undue inflammatory interactions, whereas these interactions would be less pronounced if one were to use protein-based plastics. Protein-based plastics, such as those based upon purified fish- or bovine-derived fibrinogen, are potentially less expensive—although similar to its purified human counterpart in not containing human growth factors—yet disease transmission and immuno-sensitization with repeated use are potential major drawbacks due to its xenogenic source. Analogously to plastic implants, allogeneic bone grafts also have several limitations, including high variability of graft quality from donor to donor. This variability arises from several factors, including amount of active endogenous growth factors in each donated graft, and there are no practical means for quality assessment (QA) and/or quality control (QC) of allogeneic bone graft materials with respect to these growth factors.

To date, methods and compositions previously developed for bioplastics, including but not limited to fibrin, elastin, etc., are not sufficiently adaptable for modern clinical use. Prior efforts to chemically crosslink fibrin-based bioplastics were either labor-intensive post-fabrication methods, which generally created unwanted effects such as swelling, and/or used toxic crosslinking agents such as formaldehyde. Manufacturing methods developed for certain protein-based bioplastics required high temperatures (i.e., as high as 155° C.). Such high temperature processing can preclude the use of exogenously added drugs and proteins, as well as destroy any inherent biological activity. In addition, methods for making such materials porous have not been reported or developed previously. Furthermore, steam sterilization can completely denature any biological activity in purified blood proteins. The problem of manufacturing bioplastics while avoiding the disadvantages of known processing techniques, such as high temperatures and pressures and/or difficulty in retaining desirable physical characteristics of the plastics, has not been adequately addressed.

SUMMARY OF THE INVENTION

In some embodiments, the present invention provides blood-derived plastic articles comprising at least one biological response modifier.

In some embodiments, the present invention provides blood-derived plastic articles prepared from a composition comprising (1) blood and (2) at least one crosslinking agent selected from the group consisting of iridoid derivatives, diimidates, diones, carbodiimides, acrylamides, sugars, proteins, dimethylsuberimidates, aldehydes, Factor XIII, dihomo bifunctional NHS esters, carbonyldiimide, glyoxyls, proanthocyanidin, reuterin, and mixtures thereof.

In some embodiments, the present invention provides blood-derived plastic bone tissue articles having a Young's Modulus ranging from about 0.03 GPa to about 50 GPa, measured according to ASTM Method No. D-638-03 and a compressive strength ranging from about 1 MPa to about 250 MPa according to ASTM Method No. D-695-02a, the Young's Modulus and compressive strength being determined at a temperature of about 25° C. and a pressure of about 101 KPa (about 1 atm).

In some embodiments, the present invention provides blood-derived plastic tendon tissue articles having a Young's Modulus ranging from about 0.5 GPa to about 1.5 GPa, measured according to ASTM Method No. D-638-03, a percent strain at failure ranging from about 8% to about 16% according to ASTM Method No. D-638-03, and a stiffness-ranging from about 100 N/mm to about 5000 N/mm according to ASTM Method No. D-638-03, the Young's Modulus, percent strain at failure and stiffness being determined at a temperature of about 25° C. and a pressure of about 101 KPa (about 1 atm).

In some embodiments, the present invention provides blood-derived plastic ligament tissue articles having a Young's Modulus ranging from about 100 MPa to about 1000 MPa, measured according to ASTM Method No. D-638-03 and a stiffness ranging from about 50 N/mm to about 1000 N/mm according to ASTM Method No. D-638-03, the Young's Modulus and stiffness being determined at a temperature of about 25° C. and a pressure of about 101 KPa (about 1 atm).

In some embodiments, the present invention provides blood-derived plastic cartilage tissue articles having a Young's Modulus ranging from about 1 MPa to about 250 MPa measured according to ASTM Method No. D-638-03, a percent strain at failure ranging from about 0.1% to about 1% according to ASTM Method No. D-638-03, and a stiffness ranging from about 5 N/mm to about 4000 N/mm according to ASTM Method No. D-638-03, the Young's Modulus, percent strain at failure and stiffness being determined at a temperature of about 25° C. and a pressure of about 101 KPa (about 1 atm).

In some embodiments, the present invention provides blood-derived plastic skin tissue articles comprising at least one biological response modifier, wherein the article has a Young's Modulus ranging from about 0.1 MPa to about 20 MPa, measured according to the "Skin Young's Modulus Test" described below, and an elasticity ranging from about 50% to about 100% according to the "Elasticity Test" described below, the Young's Modulus and elasticity being determined at a temperature of about 25° C. and a pressure of about 101 KPa (about 1 atm).

In some embodiments, the present invention provides blood-derived plastic skin tissue articles prepared from components comprising (1) blood and (2) at least one crosslinking agent selected from the group consisting of iridoid derivatives, diimidates, diones, carbodiimides, acrylamides, sugars, proteins, dimethylsuberimidates, aldehydes, Factor XIII, dihomo bifunctional NHS esters, carbonyldiimide, glyoxyls, and dimethylsuberimide and mixtures thereof, wherein the article has a Young's Modulus ranging from about 0.1 MPa to about 20 MPa, measured according to the "Skin Young's Modulus Test" described below, and an elasticity ranging from about 50% to about 100% according to the Elasticity Test described below, the Young's Modulus and elasticity being determined at a temperature of about 25° C. and a pressure of about 101 KPa (about 1 atm).

Methods of preparing and using the above articles also are provided.

In some embodiments, the present invention provides methods for assessing the concentration of a biological response modifier in an article comprising: (a) providing a range of acceptable concentrations of a pre-determined biological response modifier for a batch of blood to be used to prepare an article; (b) determining the concentration of a predetermined biological response modifier in a blood batch to be used to prepare an article; and (c) comparing the concentration determined in (b) to the range of acceptable concentrations obtained from (a) to determine if the concentration determined in (b) is above or below the range of acceptable concentrations determined in step (a).

In some embodiments, the present invention provides methods for making a blood-derived plastic article comprising: (a) collecting a quantity of blood; (b) clotting said blood; (c) drying said clotted blood; and (d) contacting a quantity of the clotted dried blood with at least one plasticizer to make a bioplastic dough, and shaping and heating said bioplastic dough to make a blood-derived plastic article.

In some embodiments, the present invention provides a system for preparing blood-derived plastic articles, comprising: a dryer for at least partially drying blood; a powderizing device, such as a powder miller, for milling the at least partially dried blood received from the drying apparatus to form a blood powder; a mixer for mixing the blood powder with at least one plasticizer to form a molding composition; and a compression molding apparatus comprising at least one mold for receiving the molding composition from the mixer and a vacuum degasser for removing gas from the molding composition during molding.

In some embodiments, the present invention provides methods for promoting healing of a skin wound comprising: applying to the skin wound surface an effective amount of a blood-derived plastic article, wherein the blood-derived plastic article comprises at least one biological response modifier.

In some embodiments, the present invention provides methods for promoting healing of a tissue wound or defect comprising: applying to the tissue wound or defect an effective amount of a blood-derived plastic article, wherein the blood-derived plastic article comprises at least one biological response modifier.

In some embodiments, the present invention provides methods for providing a resorbable graft to a graft position in a subject, comprising: inserting a blood-derived plastic article into a graft position in a subject, wherein the blood-derived plastic article comprises at least one biological response modifier.

In some embodiments, the present invention provides methods for delivering stem cells to a tissue of a subject, comprising: contacting a blood-derived plastic article comprising stem cells with a tissue of a subject.

In some embodiments, the present invention provides methods for connecting a first portion of a tissue with a second portion of a tissue, comprising: contacting at least one blood-derived plastic article selected from the group consisting of a suture, staple and barb with a first portion of a tissue with a second portion of a tissue, such that the first portion of the tissue and the second portion of the tissue are connected.

In some embodiments, the present invention provides methods for forming a blood-derived plastic film, comprising: (a) drying a blood-derived composition under vacuum to reduce the water content thereof and form an at least partially dried composition; and (b) shaping the at least partially dried composition into a film.

In some embodiments, the present invention provides methods for forming a blood-derived plastic article, comprising: (a) lyophilizing a blood-derived composition to reduce the water content thereof and form an at least partially dried composition; (b) mixing the at least partially dried composition with at least one plasticizer to form a mixture; and (c) shaping the mixture into a blood-derived plastic article.

DETAILED DESCRIPTION

Figure 1:
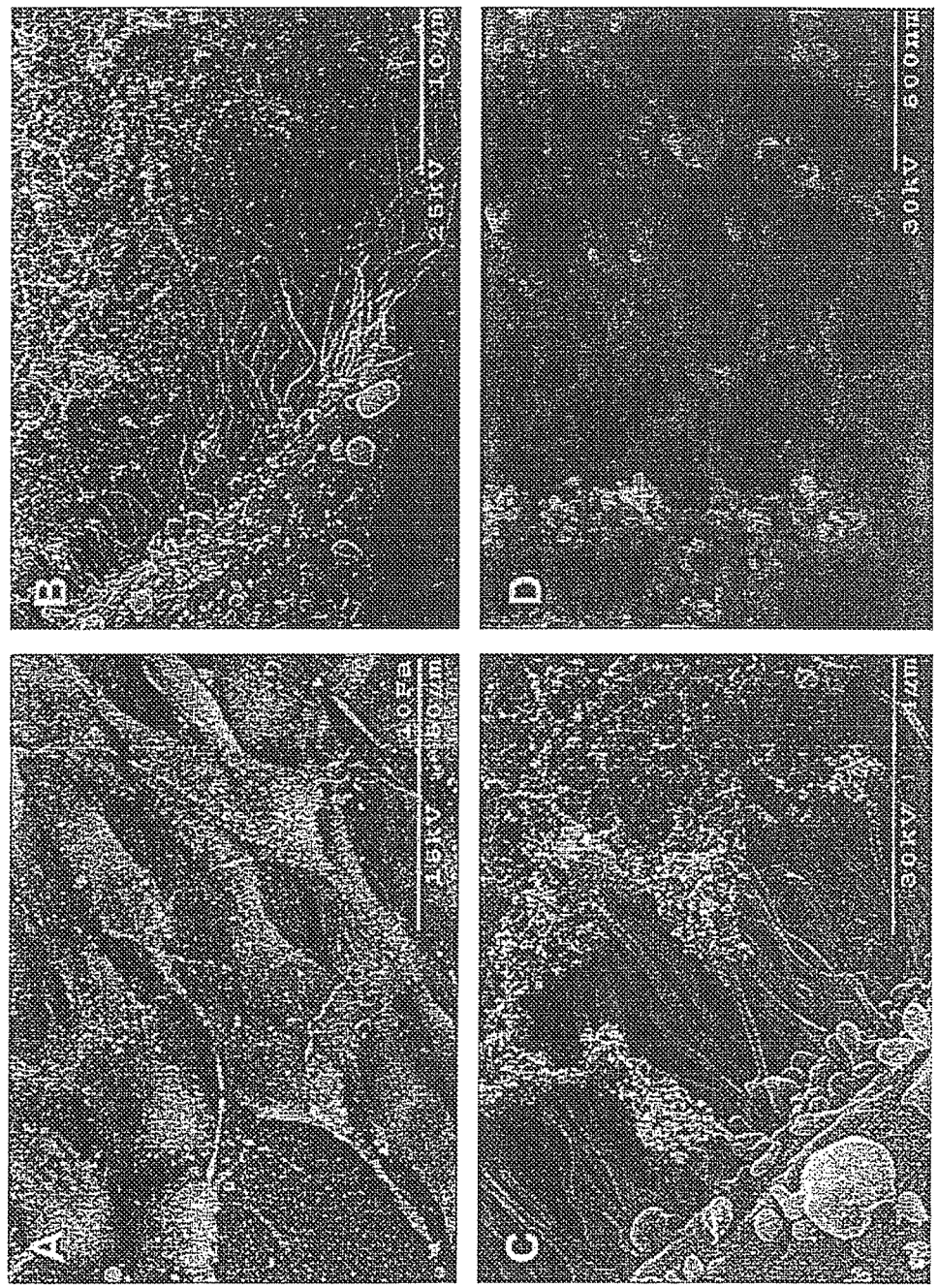
FIG. 1 depicts electron micrographs taken after osteoblastic precursor cells were cultured on plasma-based plastics (PBPs) and then monitored for subsequent cell interactions using scanning electron microscopy.

Other than in the operating examples, or where otherwise indicated, all numbers expressing quantities of ingredients, thermal conditions, and so forth, used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Furthermore, when numerical ranges of varying scope are set forth herein, it is contemplated that any combination of these values, inclusive of the recited values, may be used.

Also, it should be understood that any numerical range recited herein is intended to include all sub-ranges subsumed therein. For example, a range of "1 to 10" is intended to include all sub-ranges between and including the recited minimum value of 1 and the recited maximum value of 10, that is, having a minimum value equal to or greater than 1 and a maximum value of equal to or less than 10.

As used herein, the phrase "reaction product of" means chemical reaction product(s) of the recited components, and can include partial reaction products as well as fully reacted products.

As used herein, the term "composition" is intended to encompass a product comprising the specified ingredients in the specified amounts, as well as any product which results, directly or indirectly, from combinations of the specified ingredients in the specified amounts.

As used herein, "formed from" or "prepared from" denotes open, e.g., "comprising," claim language. As such, it is intended that an article "formed from" or "prepared from" a list of recited components be an article comprising at least the recited components or the reaction product of at least the recited components, and can further comprise other non-recited components used during the article's formation or preparation.

As used herein, the term "polymer" means a substance, typically of large molecular mass, comprising structural units or monomers. Polymers can be biological or natural materials, such as proteins, DNA, RNA, starches, fibrin and collagen, or synthetic materials, and are meant to encompass oligomers, homopolymers and copolymers. The term "prepolymer" means a compound, monomer or oligomer used to prepare a polymer, and includes without limitation both homopolymer and copolymer oligomers. The term "oligomer" means a polymer consisting of only a few monomer units up to about ten monomer units, for example a dimer, trimer or tetramer.

As used herein, the term "elastomer" refers to a polymeric material which at room temperature is capable of repeatedly recovering in size and shape after removal of a deforming force. In some embodiments, an elastomer is a material which can be repeatedly stretched to twice its original length and will repeatedly return to its approximate length on release of the stress.

As used herein, "plastic" refers to any substance, such as organic, synthetic, and/or processed materials that comprise polymers and can be made into structures such as 3-dimensional constructs and 2-dimensional constructs, such as, for example, films, sheets, laminates, filaments, and similar structures. See, for example, U.S. Pat. No. 6,143,293. As used herein, "hard plastic" refers to a plastic that tends to break in response to sufficient deformation and, thus, has small plastic and/or elastic deformation range; whereas, the term "soft plastic" refers to a plastic that readily deforms under stress without breaking, and, thus, has a large plastic and/or elastic deformation range.

As discussed above, there is a long-felt need for articles for biological applications, such as tissue grafts or tissue repair, having, inter alia, good biocompatibility, biodegradability, ease of manufacture and/or low cost. Also, it would be desirable to provide such articles having biologically active response modifiers, such as hormones, growth factors, and extracellular matrix molecules, and/or capability for drug delivery. Articles having the ability to respond to the local cellular milieu also are needed, with or without spatial patterns in the overall construct or sheet to provide such responses where desired. Also, articles are needed having desired physical properties, such as density, porosity, resorbability, and/or mechanical properties which are compatible with the biological environment into which such an article is to be placed. More reliable, cost-effective substitute tissue and graft materials have remained an illusive yet important clinical goal.

In some embodiments, the present invention provides blood-derived plastic articles which can be useful for biological applications, such as wound or tissue repair; tissue grafts such as bone grafts, tendon grafts, ligament grafts, or skin grafts; nerve guides; prosthetics/tissue interfaces; corneal grafts; plates; screws; fixtures; guides; sutures; clips; staples; barbs; resurfacing materials; tendon repair; and scaffolds for tissue engineering, for example for cell delivery such as stem cell delivery, to name a few. As used herein, the term "tissue" refers to an aggregation of similarly specialized cells united in the performance of a particular function. Tissue is intended to encompass all types of biological tissue including both hard and soft tissue, including connective tissue (e.g., hard forms, such as osseous tissue or bone) as well as other muscular or skeletal tissue.

The articles of the present invention can possess one or more of the following desirable characteristics: biocompatibility of the materials with the host or subject; the ability of the materials to degrade in relation to tissue regeneration; the binding of growth factors to the materials disclosed herein, which thereby helps minimize the dosages needed to produce therapeutic results; the ability to easily engineer the mechanical properties (e.g., ranging from elastic to rubbery to hard) of the materials; the ability to easily store the materials for off-the-shelf usage; the ability to easily shape the materials at a time and a place where the materials will be fabricated and/or clinically applied (e.g., a blood bank, an operating room, a battlefield, etc.); the ability of the article to resisting tissue prolapse at the implantation site; the ability to modulate the physiological response to the implanted materials by incorporating other materials into the base material; and the ability to select blood donors of predetermined age or other desired characteristic to provide articles having predetermined biological characteristics.

Allogeneic transplant materials, such as bone grafts, have several limitations, including high variability of graft quality from donor to donor. This variability arises from several factors, including amount of active endogenous growth factors in each donated graft, and there is no simple means for quality assessment and/or quality control of allogeneic bone grafts with respect to such growth factors. In contrast, the blood-derived plastic articles of the present invention can be prepared from pooled and processed allogeneic blood plasma from many donors which can homogenize the material constituents of the plasma, and the amount and/or types of growth factor(s) as well as other biological components contained therein, can be readily assessed for quality analysis and/or quality control as discussed below.

In some embodiments, blood-derived plastic articles of the present invention are prepared from a composition comprising whole blood and other components, as discussed in detail below. As used herein, "blood-derived" means prepared from whole blood or blood components, such as plasma or serum.

In some embodiments, plastic articles of the present invention are prepared from a composition comprising blood plasma and other components, as discussed in detail below. As used herein, "blood plasma-derived" means prepared from blood plasma.

"Whole blood" is a body fluid (technically a tissue) that is composed of blood cellular components suspended in a liquid called blood plasma. Blood cellular components include red blood cells (also called RBCs or erythrocytes), white blood cells (including both leukocytes and lymphocytes) and platelets (also called thrombocytes). As used herein, "blood" generally means whole blood or any fraction thereof, such as plasma or serum.

"Plasma" is defined as the fluid portion of human blood that has been collected, stabilized against clotting and separated from the red blood cells. Plasma can be obtained by separating plasma from blood collected from blood donors or by plasmapheresis. Plasma may be obtained from whole blood. Blood plasma is essentially an aqueous solution containing about 92% water, about 8% blood plasma proteins (such as serum albumin, blood clotting factors, immunoglobulins (antibodies)), various other proteins, electrolytes, such as sodium and chloride, hormones, xymogens, proteases, protease inhibitors and trace amounts of other materials. "Serum" is defined as blood plasma from which the clotting proteins have been removed, i.e., without fibrinogen and other clotting factors. A large percentage of the proteins remaining are albumin and immunoglobulins.

In some embodiments, the blood plasma can be "platelet-rich" or "PRP", i.e., pre-treated prior to mixing with other components of the composition to increase the concentration of platelets compared to the concentration of platelets of the blood plasma at baseline prior to such treatment. Platelet-rich plasma can be prepared by centrifugation and may have at least 250,000 platelets per microliter. In some embodiments, the blood plasma can be platelet-poor. "Platelet-poor" plasma is a portion of the plasma fraction of blood having a platelet concentration below baseline. Fresh frozen plasma ("FFP") is technically the same as platelet-poor plasma.

One embodiment of the present invention is a method of manufacturing autologous bioplastics by processing a patient's own donated blood plasma—and products produced thereby. A typical method of making such an autologous PBP (plasma-based plastic) is as follows. Blood is collected prior to surgery. The blood is spun down to obtain platelet-rich plasma (PRP) and/or platelet poor plasma (PPP) and/or serum, or comparable methods such as whole blood collection or via apheresis are used to collect plasma from the patient without having to collect whole blood. The plasma is then clotted with calcium, thrombin or other known clotting agents, and the clotting when performed on platelet-rich plasma forms a platelet-rich plasma gel. To make rubbery-to-hard plastics, the platelet-rich plasma gel is first processed into a powder by drying it (this can include first removing any retained serum or not, although it is also possible to use only serum by drying it into a powder) and then ball milling or grinding or other powdering techniques. The drying step may or may not include lyophilization, but plasma dried "through the gel phase" for use in elastomers generally should not be lyophilized if possible (see below). Alternatively, a serum-free powder can be formed by first removing serum from the gel by spinning and then drying and comminuting the remaining plasma. In general, then, the present invention can use whole plasma or plasma from which one or more constituents has been removed as desired (even to the point of only serum's remaining).

The source of blood (whole blood or its components such as blood plasma or serum) used to prepare the articles of the present invention can include humans and other mammalian species, for example, primates, rodents and livestock such as sheep, goat, pig, horse, dog and cattle. The blood can be from autologous sources or allogeneic sources. As used herein, "allogeneic" means that the blood is taken from different individuals within the same species.

In some embodiments, the source of blood can be donors between about 18 and about 65 years of age, or between about 18 and about 30 years of age, or between about 18 and about 25 years of age, or about 30 years of age or less. In some embodiments, the source of blood can be either female donors or male donors, or both.

The blood plasma used in the present invention can be obtained from blood using conventional methods such as centrifugation, sedimentation and filtration. Centrifugation can be carried out under any conditions well known to those skilled in the art as suitable to sediment blood cells (such as red and white blood cells) and cell fragments (such as platelets), for example, at about 2800 μm for about 10 minutes. The supernatant plasma can be easily separated from the centrifuged cells by conventional techniques, for example by passing the supernatant plasma through a suitable filter, such as a microporous membrane.

The blood can be fresh liquid blood, or solid or powdered blood. In some embodiments, the blood can be at least partially dried or essentially fully dried, if desired. In some embodiments, the dried blood has a water content of less than about 30 weight percent on a basis of total weight of the dried blood, or less than about 25 weight percent, or less than about 20 weight percent, or less than about 15 weight percent, prior to combination with the other components used to form the article (prior to mixing the composition or dough). In some embodiments, the dried blood has a water content of about 1 to about 25 weight percent on a basis of total weight of the dried blood, or about 5 to about 15 weight percent, or about 8 to about 12 weight percent, or about 8 to about 10 weight percent, prior to combination with the other components used to prepare the article.

The water content can be determined by various methods, for example as follows: pre-weigh three 1.5 mL microfuge tubes that have two small holes placed in the lids with a needle. Add approximately 100 mg of dried blood or plasma powder to the tube and record the mass. Place the tubes in an 80° C. oven for 48 hours. Remove the tubes, allow to cool to room temperature (about 25° C.), and weigh the tubes. Subtract the dried blood or plasma powder mass from the original powder mass, divide that value by the original powder mass, and multiply by 100%. The average of the percents obtained from the three microfuge tubes is the average % mass of water in the sample, i.e., water content.

The composition or dough is the combination of blood, plasticizer (if present) and any other components that are mixed prior to plastification processing. In some embodiments, the blood can comprise water which can function as a plasticizer. Alternatively or additionally, in some embodiments the composition can comprise one or more plasticizers such as are discussed in detail below.

In some embodiments, the blood is dried through the gel phase, by removing a portion of the water that is inherent from the original plasma clot which can represent about 0.1 to greater than about 25% by weight of the starting material. As used herein, the phrase "dried through the gel phase" means that the dried blood has a water content of about 0.01 to about 25 weight percent, or about 0.01 to about 10 weight percent, or about 0.01 to about 5 weight percent based upon total weight of the dried blood.

In some embodiments, the average particle size of the at least partially dried blood is less than about 1000 microns (μm) prior to mixing with other components of the composition, or less than about 500 μm, or less than about 150 μm, or less than about 38 μm, or about 1 μm to about 500 μm, or about 38 μm to about 500 μm, or about 38 μm to about 150 μm.

In some embodiments in which the average particle size of the particles is greater than one micron, the average particle size can be measured by mesh sieving or according to known laser scattering techniques. For example, the average particle size of such particles is measured using a Horiba Model LA 900 laser diffraction particle size instrument, which uses a helium-neon laser with a wavelength of 633 nm to measure the size of the particles and assumes that the particle has a spherical shape, i.e., the "particle size" refers to the smallest sphere that will completely enclose the particle.

In some embodiments in which the size of the particles is less than or equal to one micron, the average particle size can be determined by visually examining an electron micrograph of a transmission electron microscopy ("TEM") image, measuring the diameter of the particles in the image, and calculating the average particle size based on the magnification of the TEM image. One of ordinary skill in the art will understand how to prepare such a TEM image. The diameter of the particle refers to the smallest diameter sphere that will completely enclose the particle.

The blood can be treated prior to incorporation into the composition, for example by fresh-frozen preparation, cryoprecipitated preparation, lyophilized preparation or concentrated preparation. Fresh-frozen plasma can be obtained by centrifuging the blood at about 2,000 rpm for about 10 minutes to separate out blood cells and cell fragments and freezing the remaining liquid portion at the temperature of from about −18° C. or lower, or about −18° C. to about −40° C. The centrifugation can be carried out within six hours of blood collection. For use, the fresh-frozen plasma can be thawed out in a warm water bath at a temperature of about 30° C. to 37° C. Cryoprecipitated plasma can be obtained by thawing fresh-frozen plasma at a temperature of 4° C. to form white precipitate (cold precipitated protein), isolating the formed precipitate and refreezing it at a temperature of about −18° C. to −40° C. For use, the cryoprecipitated preparation can be thawed out by refrigerating at a temperature of from 1° C. to 6° C. overnight.

In some embodiments, the blood can be obtained from commercial sources, such as blood banks. These preparations are derived from units of human blood or blood plasma which have been tested to elicit no antigen-antibody reaction, for example, non-reactive for antibodies to hepatitis B surface antigen (HBsAg) and hepatitis C (HCV) antibody and negative for antibodies HIV-1 and HIV-2 viruses. All units of blood plasma or serum used to prepare such preparations are certified free of pathogens.

To reduce the potential risk of transmission of infectious agents, the preparation may be treated with an organic solvent/detergent mixture, such as tri(n-butyl)/phosphate/polysorbate 80 designed to inactivate enveloped viruses such as HIV, hepatitis B and HCV. The inactivation and removal of viruses can be enhanced by nanofiltration. In some embodiments, the plasma can be prepared by pasteurization of a liquid plasma fraction. Alternatively, the whole blood can be purified and the resultant plasma can be powdered by heating, lyophilization or other suitable drying techniques.

In some embodiments, the plasma is at least partially or essentially fully clotted. The plasma can be clotted with calcium, thrombin or other known clotting agents, and the clotting, when performed on platelet-rich plasma, can form a platelet-rich plasma gel. One skilled in the art can readily determine appropriate amounts of clotting agents and suitable conditions for clotting.

In some embodiments, the blood-derived plastic articles are biocompatible with the subject upon which the article is intended to be contacted. The term "biocompatible" refers to the absence of stimulation of a severe, long-lived or escalating contrary or adverse biological response to an implant or coating, and is distinguished from a mild, transient inflammation which typically accompanies surgery or implantation of an acceptable biocompatible material into a living organism. Examples of suitable subjects that can be treated according to the methods of the present invention include mammals, such as humans or dogs, and other non-mammalian animals.

In some embodiments, the blood-derived plastic articles can be biodegradable or bioerodible, i.e., degradable in response to the subject tissues' proteolytic processes. As used herein, "biodegradable" and "bioerodible" refer to the dissolution of a substance, such as implant or coating, into constituent parts that may be metabolized or excreted, under the conditions normally present in a living tissue. In some embodiments, the rate and/or extent of biodegradation or bioerosion can be controlled in a predictable manner.

In some embodiments, the present invention provides blood-derived plastic articles comprising at least one (one or more) biological response modifiers. The biological response modifier(s) can be present in the blood used to prepare the article, added to the blood and other components of the composition prior to or during formation of the plastic article, and/or the plastic article can be post-treated with a biological response modifier, for example by coating with or immersion into a composition comprising the biological response modifier(s).

As used herein, "biological response modifier" means any protein, glycoprotein, sugar, polysaccharide, lipid, DNA, RNA, aptamer, peptide, hormone, vitamin and other such substance, which when introduced into a subject is capable of eliciting a biological response, and includes hormones, cytokines, growth factors, steroids, genes, genetically modified organisms, such as viruses and bacteria, extracellular matrix molecules and the like, and mixtures thereof. The term "hormone" refers to any molecule which acts as a biochemical messenger that regulates physiological events in living organisms, and includes growth factors and cytokines.

Examples of suitable biological response modifiers include interleukins (IL), such as IL-1, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, isoforms thereof and others; interferons such as interferon alpha, beta, gamma and others; growth factors, such as platelet derived growth factors (PDGF), acidic and basic fibroblast growth factors including FGF-1 and FGF-2, transformation growth factors beta (TGF-beta, e.g. TGF-beta-1, TGF-beta-2 and TGF-beta-3), insulin like growth factors (IGF, e.g., including IGF-I and IGF-II), epidermal growth factors (EGF, e.g., EGF and heparin binding EGF), platelet-derived angiogenesis factors (PDAF), platelet-derived endothelial growth factors (PDEGF), tumor necrosis factor-alpha (TNF-.alpha.), tumor necrosis factor-beta (TNF-.beta.), vascular endothelial growth factors (VEGF), epithelial cell growth factors (ECGF), granulocyte-colony stimulating factors (G-CSF), granulocyte-macrophage colony stimulating factors (GM-CSF), nerve growth factors (NGF), neurotrophins, erythropoietin (EPO), thrombopoietin (TPO), myostatin (GDF-8), growth differentiation factor-9 (GDF9), hepatocyte growth factors (HGF), platelet factors, isoforms thereof, etc.; antibodies; bone morphogenetic proteins (BMPs), such as BMP-2, BMP-4, and BMP-7; extracellular matrix molecule such as osteocalcin, osteonectin, fibrinogen, vitronectin, fibronectin, thrombospondin 1 (TSP-1), and bone sialo-protein (BSP), proteoglycans; metalloproteases or prometalloproteases and inhibitors thereof; angiotensin converting enzyme inhibitors; plasminogen and tissue plasminogen activators (TPA), including anisoylated plasminogen activator (TPA) and anisoylated plasminogen-streptokinase activator complex (APSAC) and inhibitors thereof; xymogens such as prothrombin, plasminogen, prokallikrien, proelastase, and procollagenase; proteases such as thrombin, plasmin, kallikrien, elastase, and collagenases; protease inhibitors such as aprotinin, alpha 1-antitrypsin, alpha 2-microglobulin, alpha 2-antiplasmin, anti-thrombin and tissue inhibitor of metalloproteases (TIMP1); RNA and DNA in its various forms to modify gene expression and function; cytokines including chemotactic cytokines (chemokine), protein-based hormones such as parathyroid hormone, engineered hormones, steroid-based hormones, such as estrogen, pregnenolone, aldosterone, estradiol, cortisol, testosterone, progesterone, etc.; peptide hormones, such as insulin, parathyroid hormone related peptide, luteinizing hormone (LH), adrenocorticotropic hormone (ACTH), follicle stimulating hormone (FSH), and angiotensin II/III; synthetic steroids including, but not limited to, glucocorticoids, such as prednisone, dexamethasone, triamcinolone, etc., mineralocorticoids, such as fludrocortisone, Vitamin D derivatives, such as dihydrotachysterol, synthetic androgens, such as oxandrolone, decadurabolin, etc., synthetic estrogens such as diethylstilbestrol (DES); synthetic progestins, such as norethindrone and medroxyprogesterone acetate; and mixtures thereof. Further examples of suitable growth factors and bone morphogenetic proteins from platelets are discussed in Eppley, B. L. et al., "Platelet-Rich Plasma: A Review of Biology and Applications in Plastic Surgery", Plast. Reconstr. Surg. 118(6) pp. 147e-159e (2006) and Sipe J. B., et al., "Localization of Bone Morphogenetic Proteins (BMPs)-2, -4, and -6 within Megakaryocytes and Platelets", Bone 35(6). pp. 1316-22 (2004), incorporated by reference herein.

In some embodiments, the biological response modifier is a bioactive protein selected from the group consisting of hormones, growth factors, cytokines, extracellular matrix molecules and mixtures thereof, such as are discussed above.

As discussed above, the biological response modifier(s) can be present in the blood used to prepare the composition, or added to the other components of the composition as a separate component prior to formation of the article, or added by post-treatment. In some embodiments, the amount of biological response modifier present in the blood or composition can range from about 1 picogram per gram of composition to about 20 milligrams per gram of composition, or about 1 nanogram per gram of composition to about 1 milligram per gram of composition, or about 1 microgram per gram of composition to about 1 milligram per gram of composition. The presence and/or amount of biological response modifier present in the blood or composition can be determined by assays and analytical methods well known to those skilled in the art, for example immunoassays including visual or fluorescent-based assays such as ELISA (enzyme-linked immunosorbent assay) and radioactive-based assays such as RIA (radioimmunological assay) or IRMA (immunoradiometric assay).

In some embodiments, the biological response modifier is biologically active when present in the article, i.e., present before or after formation of the article for example by compounding or plasticizing. The level of biological activity can be reduced during the formation of the article, however, at least some biological activity is preferably retained.

In some embodiments, the amount of biological response modifier present in the article can range from about 1 picogram per gram of article to about 20 milligrams per gram of article, or about 1 nanogram per gram of article to about 1 milligram per gram of article, or about 1 microgram per gram of article to about 1 milligram per gram of article.

The presence and/or amount of biological response modifier present in the blood, composition or article can be determined by assays and analytical methods well known to those skilled in the art, such as are discussed below. Various proliferation assays, commonly known and standardized in the art, can be used to determine cell proliferation responses. For example, a radiological proliferation assay can be used for determination of biological activity of articles or compositions of the present invention. Cells (NIH 3T3 mouse fibroblasts, for example) are seeded into wells of a 24 well cell culture plate at 20,000 cells per well in serum media. Twenty four hours later the growth media is replaced by serum-free media. Twenty four hours later the serum-free media is replaced with serum-free media conditioned by soaking with blood, composition or crushed blood-based biopolymer for 24 hours. Positive controls consist of cells grown in serum media and negative controls of cells grown in serum-free media. Twenty four hours later 2.5 µCi of tritiated thymidine is added per well and four hours later the cells are washed and the incorporated thymidine isolated and counted using protocols known in the art. To determine blood-based biopolymer bioactivity resulting in cellular proliferation over the negative control, statistical analyses can be performed using multiple analysis of variance (ANOVA) and Tukey's post-hoc test for multiple comparison analysis, with a significance level of $p<0.05$.

The presence of growth factors, among other bioactive factors, within a sample can be detected through the use of a variety of commercially available immunoassays, such as RIA, ELISA or IRMA. These assays are available for a large number of human bioactive proteins such as VEGF, BMP-2, TGF-beta, and PDGF, for example.

Various differentiation assays commonly known and standardized in the art, such as gene expression-based assays or protein expression-based assays, can be used to determine the bioactivity of certain hormones (including cytokines, growth factors, etc.) to induce cellular differentiation. For example, BMP-2 will induce C2C12 mouse progenitor cells to differentiate into bone cells, as evidenced by the induction of C2C12 alkaline phosphatase expression. C2C12 cells can be seeded onto plasma-based biopolymers (5 mm.times.5 mm in area) with 2 mL of 60,000 cells/mL in a 12 well plate in serum media. Cells seeded into an empty well with serum media and cells in an empty well with serum media plus 100 ng/mL BMP-2 serve as negative and positive controls, respectively. Forty eight hours post-seeding, the cells are stained for alkaline phosphatase using a commercial kit. Alternatively to seeding onto biopolymer plastics, cells can be incubated in serum-free media conditioned by soaking with crushed plasma-based biopolymer for 24 hours.

In some embodiments, the biological response modifier is heat-sensitive. As used herein, "heat-sensitive" means any compound which when heated beyond 50° C. becomes biologically inactive. Thus, the term "heat-sensitive" compound encompasses any compound, such as biological response modifiers, antigens, drugs, hormones, tracers, labeled compounds, which lose biological activity at a temperature greater than about 50° C., or greater than about 80° C., by any means including melting, decomposition, denaturation, etc. In some embodiments, low temperature processing of the composition to form the plastic article can be conducted at a temperature of less than about 50° C., or less than about 65° C., or less than about 80° C., or about 55° C. to about 65° C., or about 60° C.

In some embodiments, the composition from which the article is prepared can further comprise at least one crosslinking agent for crosslinking or gelling various crosslinkable groups of the blood and/or with other components of the composition. Suitable cross-linking agents may be physical or chemical. Examples of suitable chemical crosslinking agents include iridoid derivatives (such as genipin (Methyl (1R,2R,6S)-2-hydroxy-9-(hydroxymethyl)-3-oxabicyclo [4.3.0]nona-4,8-diene-5-carboxylate), diimidates, diones (e.g., 2,5-hexanedione), carbodiimides, (e.g., 1-ethyl-[3-(dimethylaminopropyl)]carbodiimide) (abbr., EDC), acrylamides (e.g., N,N'methylenebisacrylamide), sugars (e.g., ribose and fructose), proteins (e.g., enzymes, such as transglutaminase Factor XIII), dimethylsuberimidates, aldehydes (e.g., glutaraldehyde, and formaldehyde, formaldehyde sodium bisulfite), dihomo bifuntional NHS esters (e.g., di NHS-esters of dicarboxylic acid comprising 1-20 intervening carbons), carbonyldiimide; glyoxyls; proanthocyanadin, reuterin (2-hydroxy-propanal), similar cross-linking agents and mixtures thereof.

Chemical cross-linking agents can be solids (e.g., powders) or liquids. Examples of cross-linking agents which are solids include, genipin, dihomo bifuntional NHS esters, and formaldehyde sodium bisulfite. Examples of liquid crosslinking agents include formaldehyde, glutaraldehyde, etc. In some embodiments, the article comprises monoaldehyde or polyaldehyde cross-linked amines; and/or pyran cross-linked amines. As used herein "cross-linked amine" refers to any bridging bond between two polymers comprising nitrogen, such as the product of aldehyde cross-linking (i.e., an imine or an eneamine), or product of an ester cross-link, or an amide, or any other similar bond. Physical cross-linking agents include, for example, electromagnetic radiation, such as ultraviolet light, heat, microwaves, etc. Cross-linking may occur before or after formation of the article. Mixtures of any of the above crosslinking agents can be used.

In some embodiments, the crosslinking agents are selected from the group consisting of iridoid derivatives, diimidates, diones, carbodiimides, acrylamides, sugars, proteins that are chemically different from the bioactive protein, dimethylsuberimidates, aldehydes, Factor XIII, dihomo bifunctional NHS esters, carbonyldiimide, glyoxyls, proanthocyanadin, reuterin, dimethylsuberimide and mixtures thereof.

Solid cross-linking agents can be active, even prior to hydration, for example, where the polymer contains residual water and/or amino groups. Thus, where a solid crosslinking agent is used, it can be active prior to hydration or, in the alternative, upon exposure to water. For example, in some embodiments the solid cross-linking agent, genipin, is incorporated into the polymer admixture and subsequently allowed to be activated by water which is either already in the polymer, blood or composition and/or which is absorbed when the subsequently formed polymer matrix is in a hydrated liquid environment. Because water is either already in the matrix (e.g., because of residual water in the matrix) or diffuses into a polymer matrix (e.g., from immersion into a hydrated environment), cross-linking can occur throughout the material. This method obviates the problem often observed with liquid crosslinking agents, which cross-link as they diffuse into the gel, creating a stiff outer shell, while the internal part of the gel swells with water since it has not been exposed to the cross-linking agent due to the slow diffusion of the cross-linking agent. Such inhomogeneity can create pressure within the structure, sometimes leading to cracking and deformation. Thus in some embodiments, incorporation of the crosslinker into the composition as a solid, such as genipin, can be used. Genipin is a pyran hydrolytic product of geniposide, and is capable of forming cross-links with amines and with itself. Genipin is a cross-linking agent of low toxicity, and, thus, better suited for use in numerous biomedical applications, since many other cross-linking agents such as glutaraldehyde can be toxic to cells. In addition, genipin conjugates can turn a brown and/or a blue color and fluoresce, thus allowing visual monitoring of the extent and positions of the cross-linking, in real-time.

Genipin can be added as a powder up to about 2% by weight or more of the dried blood weight, prior to dough mixing and plasticizing. Genipin powder (known in the art) can be solubilized in alcohol, such as ethanol, methanol, glycerol, isopropanol, propylene glycol, or any of the di-, tri- or tetra-polyethylene glycols. Also, since an alcohol can be used to sterilize the plasma powder, genipin or other crosslinking agents may be added to the alcohol during sterilization, and can be retained in the bioplastic dough while the alcohol fraction is removed. It also should be understood that genipin in solution can be admixed into the bioplastic dough, or genipin in solution can be infused into a plasma gel, but it may also be incorporated as a dry powder with any of the present bioplastic ingredients at any step of processing. Other crosslinkers, both water- and alcohol-soluble, known in the art may be substituted.

The amount of crosslinking agent used in the composition can range from about 0.01 to about 20 weight percent, or about 0.1 to about 20 weight percent, or about 0.1 to about 10 weight percent, or about 0.1 to about 1 weight percent, on a basis of total weight of the composition.

As used herein, the term "cross-link" or "crosslink" as used in connection with a composition, means that any crosslinking agent in the composition has at least partially reacted with itself and/or with functional groups of components of the composition, creating crosslinks therein. In some embodiments, the degree of crosslinking, i.e., the degree of total functional groups of the crosslinking agent that have reacted within the composition, ranges from about 50% to about 100% of complete crosslinking where complete crosslinking means full reaction of the crosslinking agent in the composition. In other embodiments, the degree of crosslinking ranges from about 75% to about 100% or about 90% to about 100% of full crosslinking. One skilled in the art will understand that the presence and degree of crosslinking, i.e., the crosslink density, can be determined by a variety of methods, such as Fourier Transform Infrared Spectroscopy (FTIR), mechanical testing, gel chromatography, etc.

As used herein, the term "cure" as used in connection with a composition, e.g., "composition when cured" or a "cured composition", refers to the toughening or hardening of the composition, brought about by physical or chemical means, such as by chemical components of the composition having reactive functional groups, ultraviolet radiation, electron beam (EB), heat, and/or pressure. After reaction of most of the reactive groups occurs within a composition subjected to curing conditions, the rate of reaction of the remaining unreacted reactive groups becomes progressively slower. In some embodiments, the curable composition can be subjected to curing conditions until it is at least partially cured. The term "at least partially cured" means subjecting the curable composition to curing conditions, wherein reaction of at least a portion of the reactive groups of the composition occurs, to form a partially cured composition. In some embodiments, the composition can be subjected to curing conditions such that a substantially complete cure is attained and wherein further exposure to curing conditions results in no significant further improvement in properties, such as strength or hardness.

The articles of the present invention can be in the form of a hydrogel prior to application to a subject. A "hydrogel" is defined as a substance formed when a polymer (natural or synthetic) becomes a 3-D open-lattice structure that entraps solution molecules, typically water, to form a gel. A polymer may form a hydrogel by, for example, aggregation, coagulation, hydrophobic interactions, cross-linking, salt bridges, etc. A plasma gel is a hydrogel classically formed by clotting methods well known in the art (e.g., by adding thrombin, calcium chloride, etc.). Alternatively, plasma can be formed into a hydrogel through the addition of other exogenous factors, such as crosslinkers. Where a hydrogel is to be used as part of a scaffold onto which cells will be seeded, the hydrogel should be non-toxic to the cells. The term "dehydrated" whether referring to a structure, such as a film, or a hydrogel includes any substance that has had water removed from it by any processes, and, thus, includes partially hydrated hydrogels, such as those described herein.

A "hydrogel solution" is a solute and a solvent comprising a substance that if subjected to the appropriate conditions, such as temperature, salt concentration, pH, the presence of a protease, the presence of a binding partner, etc., becomes a hydrogel or part of a hydrogel. The term "solution" in a hydrogel solution is intended to include true solutions, as well as suspensions, such as colloidal suspensions, and other fluid materials where one component is not truly solubilized.

In some embodiments, the present invention provides blood-derived plastic articles prepared from a composition comprising: (1) blood (which optionally can comprise one or more biological response modifiers and/or other components discussed below) and (2) at least one crosslinking agent selected from the group consisting of iridoid derivatives, diimidates, diones, carbodiimides, acrylamides, sugars, proteins that are chemically different from the bioactive secretory protein, dimethylsuberimidates, aldehydes, Factor XIII, dihomo bifunctional NHS esters, carbonyldiimide, glyoxyls, dimethylsuberimide, proanthocyanadin, reuterin, and mixtures thereof. Suitable blood products and crosslinking agents and amounts of the same are discussed in detail above.

Any of the compositions discussed above can further comprise at least one plasticizer in addition to any plasticizer (such as water) in the blood. Examples of suitable plasticizers include phthalate plasticizers, adipate plasticizers, trimellitate plasticizers, maleate plasticizers, sebacate plasticizers, benzoate plasticizers, plant oils, such as epoxidized vegetable oils, animal oils, mineral oils, sulfonamide plasticizers, phosphate plasticizers, water, polyalcohols, glycols, glycerol (glycerin), polyethers, acetylated monoglycerides, alkyl citrates, polymeric plasticizers and functionalized derivatives thereof, such as poly(ethylene glycol) diacrylate, and mixtures thereof. In some embodiments, the plasticizer can have reactive functional groups which are capable of polymerizing with itself, the blood and/or other composition components during mixing and/or curing of the composition. In some embodiments, the plasticizer is glycerol and/or water.

The amount of plasticizer used in the composition can range from about 0.1 to about 80 weight percent, or about 5 to about 60 weight percent, or about 10 to about 60 weight percent, or about 20 to about 50 weight percent, on a basis of total weight of the composition.

In some embodiments, the composition further comprises at least one drug. The term "drug" refers to a substance used as a medication or in the preparation of medication, including, but not limited to, a substance intended for use in the diagnosis, cure, mitigation, treatment, or prevention of a condition, such as infection, disease, or trauma. For example, a drug may include, but is not limited to, small organic molecules, complex organic molecules, inorganic elements and molecules, and the like. As used herein, the term "drug" encompasses for example, fungicides, anticoagulants, antibiotics, antivirals, anti-inflammatories, both steroidal and non-steroidal, antibodies, and other molecules. Examples of suitable drugs include analgesics; anti-infective agents such as antibiotics (for example cephalosporins; penicillins; aminoglycosides including gentamicin and neomycin; glycopeptides including vancomycin; macrolides including azithromycin and clarithromycin; quinolones including ciprofloxacin, gatifloxacin, and levofloxacin; sulfonamides; and tetracycline), antifungals (for example polyene antifungals, imidazole antifungals and triazole antifungals), and antivirals; antineoplastics such as antibiotics, antimetabolites, hormonal agonists/antagonists, androgens, immunomodulators, skin and mucous membrane agents and steroids; biologicals; blood modifiers such as anticoagulants, anti-platelet agents, colony stimulating factors, hematinics, hemorrheologic agents, hemostatics, thrombin inhibitors and thrombolytic agents; cardioprotective agents; cardiovascular agents such as adrenergic blockers, adrenergic stimulants, angiotensin converting enzyme (ACE) inhibitors, angiotensin II receptor antagonists, antiarrhythmics, antilipemic agents, beta adrenergic blocking agents, vasodilators, and vasopressors; cholinesterase inhibitors; hormones such as: anabolic steroids, androgens, estrogens and combinations, glucocorticoids and growth hormone; immunomodulators; immunosuppressives; ophthalmic preparations such as antibiotics, anti-infectives, anti-inflammatory agents and beta adrenergic blocking agents; respiratory agents such as anti-infective agents, anti-inflammatory agents, skin and mucous membrane agents such as analgesics, anti-infectives, antibiotics, antifungals, antivirals, antineoplastics, anti-cancer agents and mixtures thereof.

The drug can be administered via the article in a "therapeutically effective amount", i.e., that amount of a pharmacological or therapeutic agent that will elicit a biological or medical response of a tissue, system, or subject that is being sought by the administrator (such as a researcher, physician, clinician or veterinarian) which includes alleviation of the symptoms of the condition or disease being treated and the prevention, slowing or halting of progression of the condition, including but not limited to infection, disease or trauma.

The amount of drug used in the article can range from about 0.001 to about 10 weight percent, or about 0.001 to about 5 weight percent, or about 0.001 to about 1 weight percent, on a basis of total weight of the composition. The amount of drug used in the composition to prepare the article can be the same as is desired in the article or higher to account for loss of activity (if any) during preparation of the article. One skilled in the art can determine the amount of desired drug by routine experimentation, or for example the amount of drug used in the composition can range from about 0.001 to about 10 weight percent, or about 0.001 to about 5 weight percent, or about 0.001 to about 1 weight percent, on a basis of total weight of the composition. Alternatively or additionally, one or more drugs can be included for co-administration or delivery with the article, for example by coating or impregnating at least a portion of the article.

In some embodiments, the composition further comprises at least one stabilizer. The stabilizer may be added to the plasma constituents to protect endogenous plasma proteins during dehydration, rehydration, lyophilization and/or subsequent milling. Examples of suitable stabilizers include glycogen, sorbitol, mannitol, trehalose, maltitol, xylitol, isomaltitol, erythritol, amylose, amylopectin, inositol hexasulfate, sulfated beta-cyclodextran, betaine, nontoxic polysaccharide according to the general formula of $C_n(H_2O)_{n-1}$ where n is between 200 and 2500, antioxidants, and mixtures thereof.

The amount of stabilizer used in the composition can range from about 0.1 to about 70 weight percent, or about 0.1 to about 25 weight percent, or about 0.1 to about 10 weight percent, on a basis of total weight of the composition.

In some embodiments, the composition can further comprise at least one filler. Examples of suitable fillers include any substance incorporated into the polymer in order to provide additional structural or mechanical properties to the compositions disclosed herein, for example particulates such as calcium phosphate, tricalcium phosphate, calcium sulfate, hydroxyapatite, excipients (e.g., inert compounds acting as bulking agents, such as carboxymethylcellulose or starch), synthetic and/or naturally occurring substances, such as polysaccharides and proteins (e.g., fibrous or globular proteins), which can be, for example, inert or biologically active or inactive, and mixtures thereof. In some embodiments, the fillers can be nanoparticulates.

The amount of filler used in the composition can range from about 0.1 to about 75 weight percent, or about 5 to about 70 weight percent, or about 25 to about 60 weight percent, on a basis of total weight of the composition.

In some embodiments, the composition further comprises at least one porogen. The term "porogen" refers to any particulate incorporated into a polymer matrix, wherein the particulate can be removed by any means including dissolution or sublimation of the porogen into a liquid or gas phase. A porogen can be soluble in the aqueous phase, the organic phase, or capable of sublimation into a gas. A porogen can also comprise an encapsulated gas (i.e., $CO_2$, nitrogen, oxygen, etc.) or substance capable of releasing a gas, upon decomposition, such as, for example, sodium bicarbonate releasing $CO_2$ upon contact with an acid. Examples of suitable porogens include polyurethane, polylactic acid, polyglycolic acid, polylactic-co-glycolic acid, and polycaprolactone; a porogen soluble in an aqueous phase, such as sodium chloride; or a sublimation porogen, such as ammonium acetate, ammonium chloride, ammonium sulfate, ammonium bicarbonate, ammonium carbonate or pyridinium trifluoroacetate, and mixtures thereof. In some embodiments, the introduction of particulate ammonium acetate crystals, pre-sized to 150-250 microns, during the dough mixing phase, and following sublimation (drying under vacuum) post processing, resulted in a controlled porous plastic with a pore size of 150-250 microns.

The amount of porogen used in the composition can range from about 0.1 to about 95 weight percent, or about 20 to about 90 weight percent, or about 30 to about 75 weight percent, on a basis of total weight of the composition.

In some embodiments, the composition further comprises at least one polymeric material, including biocompatible polymeric materials such as polymeric sugars, for example polysaccharides (e.g., chitosan) and glycosaminoglycans, (e.g., hyaluronan, chondroitin sulfate, dermatan sulfate, keratin sulfate, heparan sulfate, and heparin), polymeric proteins, such as fibrin, collagen, fibronectin, laminin, and gelatin, and mixtures thereof. Examples of biocompatible, non-biodegradable polymers include, but are not limited to, polyethylenes, polyvinyl chlorides, polyamides, such as nylons, polyesters, rayons, polypropylenes, polyacrylonitriles, acrylics, polyisoprenes, polybutadienes and polybutadiene-polyisoprene copolymers, neoprenes and nitrile rubbers, polyisobutylenes, olefinic rubbers, such as ethylene-propylene rubbers, ethylene-propylene-diene monomer rubbers, and polyurethane elastomers, silicone rubbers, fluoroelastomers and fluorosilicone rubbers, homopolymers and copolymers of vinyl acetates, such as ethylene vinyl acetate copolymer, homopolymers and copolymers of acrylates, such as polymethylmethacrylate, polyethylmethacrylate, polymethacrylate, ethylene glycol dimethacrylate, ethylene dimethacrylate and hydroxymethyl methacrylate, polyvinylpyrrolidones, polyacrylonitrile butadienes, polycarbonates, polyamides, fluoropolymers, such as polytetrafluoroethylene and polyvinyl fluoride, polystyrenes, homopolymers and copolymers of styrene acrylonitrile, cellulose acetates, homopolymers and copolymers of acrylonitrile butadiene styrene, polymethylpentenes, polysulfones, polyesters, polyimides, polyisobutylenes, polymethylstyrenes, other similar compounds known to those skilled in the art, and mixtures thereof. Other biocompatible non-degradable polymers that are useful in accordance with the present invention include polymers comprising biocompatible metal ions or ionic coatings which can interact with DNA, for example gold and silver ions may be used for inhibiting inflammation, binding DNA, and inhibiting infection and thrombosis. Examples of biocompatible, biodegradable polymers include, but are not limited to, polylactic acid (PLA), polyglycolic acid (PGA), polylactic-co-glycolytic acid (PLGA), polycaprolactone, and copolymers thereof, polyesters, such as polyglycolides, polyanhydrides, polyacrylates, polyalkyl cyanoacrylates, such as n-butyl cyanoacrylate and isopropyl cyanoacrylate, polyacrylamides, polyorthoesters, polyphosphazenes, polypeptides, polyurethanes, polystyrenes, polystyrene sulfonic acid, polystyrene carboxylic acid, polyalkylene oxides, alginates, agaroses, dextrins, dextrans, and polyanhydrides. Mixtures of any of the above polymeric materials can be used.

The amount of polymeric material used in the composition can range from about 0.1 to about 90 weight percent, or about 10 to about 80 weight percent, or about 15 to about 75 weight percent, on a basis of total weight of the composition.

In some embodiments, the composition further comprises at least one tracer, labeled compound or mixtures thereof. The term "tracer" refers to any molecule that is introduced into an organism or construct and capable of being detected. For example, tracers include, but are not limited to, radioactive compounds, contrast agents, light-emitting molecules, quantum dots, fluorescent molecules, dyes, biomarkers, molecular tracers for imaging purposes (including fluorescence markers, radioactive markers, contrast agents for CT, microCT, MRI or forms of bio-imaging, and immunospecific markers), and others. As used herein, a "labeled compound" refers to any substance modified such that it (or its metabolites, such as degradation products) is detectable by any means. A labeled compound may be labeled in any manner including attachment (e.g., covalent or non-covalent) of tracers to the molecule of interest.

In some embodiments, the composition can further comprise metal ions, for example gold and silver ions can be used for inhibiting inflammation, infection and/or thrombosis. The amount of metal ions used in the composition can range from about 0.01 to about 5 weight percent on a basis of total weight of the composition.

In some embodiments, the present invention provides methods of making blood-derived plastics using blood which is at least partially clotted either before or after removal of any desired constituents, at least partially dried and optionally powdered, mixed with other components such as plasticizer, etc. as discussed above, and processed into a plastic article.

Suitable methods for clotting the blood, such as admixing with calcium, thrombin or another suitable clotting agent, are discussed above. The clotted blood can be at least partially dried to a water content as described above by a variety of methods, such as freeze drying (lyophilization), heating in a conventional oven, air-drying, etc. In some embodiments, the clotted blood is lyophilized at a temperature of less than about −18° C. In some embodiments, the clotted blood is dried at a temperature of less than about 50° C., or less than about 80° C.

In some embodiments, the clotted and dried blood can be ground into a powder or otherwise comminuted by any means known in the art, for example by milling, grinding, spray-drying, etc. In some embodiments, the average diameter of the blood powder particles can be less than about 30 mesh (i.e., about 595 microns), less than about 35 mesh (i.e., about 500 microns), less than about 100 mesh (i.e., about 149 microns), less than about 200 mesh (i.e., about 74 microns), or less than about 400 mesh (i.e., about 37 microns) or about 10 to about 800 microns.

Prior to further processing, the dried blood or powder can be treated (washed) with ethanol or propanol to sterilize it and, if desired, to remove unwanted salts from the blood by removing the wash-step alcohol.

In some embodiments, the clotted and dried blood (optionally powdered) can be mixed with other components of the composition in amounts as described above, such as plasticizer and/or crosslinking agent, in any conventional manner, for example by mixing in a container using a stainless steel stirrer for about 2 minutes to about 24 hours at a temperature of about 25° C.

In some embodiments in which a solid crosslinking agent, such as genipin, is used, the crosslinking agent can be pre-dissolved in a solvent prior to mixing with the other components of the composition. Examples of suitable solvents include alcohols such as ethanol or isopropanol. The amount of solvent used can be that amount which is sufficient to at least partially or fully dissolve the solid crosslinking agent, for example about 1 to about 200 mg of crosslinking agent per ml of solvent.

In some embodiments, the clotted and dried blood may be added to virtually any polymeric or plastic base material that will cure at the desired temperatures. In some embodiments, clotted and dried plasma, plus plasticizer (water and/or glycerol) is used to make a bioplastic material without other structural-plastic-making additives. Except for constituting materials such as powders, additives, biologics or drugs, etc., in some embodiments the present inventive compositions consist essentially of clotted and dried plasma plus plasticizer.

The composition can be formed into a plastic article by any suitable means known in the art, for example by molding, extrusion, casting or printing. In some embodiments, articles can be formed by extruding the plastic precursors through a die so that the extruded plastic is shaped as desired, for example in the shape of a film, sheet, tube, filament, rod or sheet. Extrusion can be accomplished at relatively low pressures and temperatures; under certain processing conditions the plastic may be partially or completely dehydrated by the extrusion process. After sufficient dehydration, with or without the use of osmotic membranes and/or lyophilization, the extruded material may be plasticized and, optionally, crosslinked. In some embodiments, extrusion can create an alignment, i.e., anisotropy, of the constituent molecules within the plastic and so impart certain properties, such as toughness, to the final elastomeric and/or pliant materials. In some embodiments, biological response modifiers, drugs, antigens, tracers, or other such molecules can be included in the composition or added into the bulk plastic material, such as the admixture or slurry, prior to processing. Suitable extrusion equipment is well known to those skilled in the art, for example Brabender extrusion equipment. The processing temperature used in the extruder can be uniform or vary across the extrusion zones, as desired. Examples of suitable processing temperatures can be less than about 50° C., or less than about 80° C., to preserve biological activity. Higher processing temperatures can be used, if desired.

In some embodiments, articles can be formed by molding, for example by compression molding. Suitable molding apparatus are well known to those skilled in the art. In some embodiments, the molding process can be conducted at a temperature of about 45° C. to about 150° C. at a pressure of about 5 to about 50 kpsi. The molding process can include use of a release agent to facilitate mold release. In some embodiments, the molding apparatus can include a cooperating hot press and a vacuum degasser.

Fabrication can also be by powder molding according to the following alternative method. Molds are filled with powdered materials, including the powdered plasma, and subsequently infiltrated with plasticizer such as glycerol under positive pressure. Similarly, negative pressure may be applied to the bottom of the powder bed as glycerol, or other plasticizer, is applied over the top, or a combination of both, by vacuum casting. The resulting powdered structure can be compacted by compression molding according to PCT/US06/29754.

As an alternative to molding, powdered materials can be selectively deposited, voxel-by-voxel and layer-by-layer into a mold cavity to form either homogenous or heterogenous 3D structures. Then, glycerol, or another plasticizer, can be infused into the structure under positive pressure, or by applying a negative pressure to the bottom of the powder bed as glycerol is applied over the top, or a combination of both. The resultant powdered structure may be compacted by compression molding according to PCT/US06/29754.

In some embodiments, the water content of a composition can be controlled by vacuum drying, i.e., by controlling vacuum and/or temperature so as to dehydrate the composition. Such vacuum processing techniques are especially useful for large scale processing. In some embodiments, the water content of the composition is controlled by evaporating the water under normal atmospheric pressure. Evaporative processes may be performed at any temperature. In some embodiments, the temperature used to evaporate the water is less than the temperature at which molecules incorporated into the polymer matrix would denature. This is referred to as the subcritical pressure and/or temperature for the inclusion present in a polymer matrix. In some embodiments, such processing techniques allow the polymer matrix to be loaded with a substance, such as a crosslinking agent, and subsequently formed into a structure, such as a film, without loss of bioactivity of the incorporated substance. For example, a composition can be dehydrated at various temperatures that would prevent the degradation or denaturation of heat-sensitive chemicals and proteins, e.g., at a temperature of less than 80° C., less than 70° C., less than 65° C., less than 60° C., less than 55° C., less than 50° C., less than 45° C., less than 40° C., less than 35° C., less than 30° C., less than 25° C., or room temperature, or less. Use of temperatures of less than room temperature or even less than 4° C. are also possible, such as freeze-drying of the composition. Pressure may also be regulated during the drying process. Pressures may be reduced below a normal atmosphere by any means, including use of a gel dryer connected to a vacuum source. Vacuum pressure can be less than 100 millibars, less than 50 millibars, less than 25 millibars, less than 20 millibars, less than 15 millibars, less than 10 millibars, less than 5 millibars, less than 1 millibar, or even less. Those of skill in the art recognize that by reducing the pressure and/or increasing the temperature, the drying time can be decreased. Thus, drying may occur over any time period, such as over 1 hour, 2 hours, 4 hours, 8 hours, 16 hours, 24 hours, or longer. Moreover, the drying time can be varied to allow the composition to remain partially hydrated; i.e., wherein not all of the trapped water in the composition is removed. In some embodiments, the composition can be dried on a substantially planar surface, thus creating a substantially planar film, for example by placing in a frame, and/or compressing between sheets of material that preserve the forms, such as plastic sheets. In some embodiments, the composition can be dried over a formed shape, thus creating a formed film that can be removed from the shape. In some embodiments, the composition can be dried directly onto a structure or surface and not removed, thereby creating a film coating on the structure or surface.

In some embodiments, water and plasticizer can be added before formation of the article. In some embodiments, once the water is removed from the composition, plasticizer can be added to the resulting material. In some embodiments, the addition of plasticizer can be accomplished by soaking the dehydrated material in a bath of the plasticizer. In some embodiments, tracers, and/or labeled compounds may be incorporated into the polymer matrix.

In some embodiments, the processing steps can be performed under tensile load conditions to modify subsequent biomechanical properties of the material by aligning filaments of the component material, e.g., fibrin. When plasticizer is added to the resulting material the orientation of the components of material can exhibit improved mechanical properties for application as graft substitutes for soft tissue repair including vascular, tendon and ligament tissues.

In some embodiments, the plasticizing temperature can be between about 55 to about 65° C. In some embodiments, the clotted dried blood-containing composition may be plasticized at temperatures up to about 150° C., particularly to create harder and/or denser bioplastic materials. In some embodiments, the clotted dried plasma containing admixtures of the present invention can be plasticized at suitable pressures, for example about 9 to about 25 kpsi (kilopounds per square inch), about 9 to about 15 kpsi or at least 10.7 kpsi or higher. The resulting plasma-based plastics (PBPs) of the present invention can thus be made with a range of biomechanical and degradation properties. PBPs can be used in a variety of clinical applications, including their use as substitute graft materials, drug delivery carriers, anti-adhesion and barrier membranes and scaffolds for tissue engineering. PBPs can also be used in cell culture as a non-animal source of endogenous or exogenous growth media.

Polymer molecular weight can be determined by gel permeation chromatography (GPC); bond structure by infrared (IR) spectroscopy; and toxicology by initial screening tests involving Ames assays and in vitro teratogenicity assays, and implantation studies in animals for immunogenicity, inflammation, release and degradation studies.

In some embodiments, the plastic articles are capable of deformation. Such plastics may be hard or soft plastic, depending on intended use. These polymers may be shaped, machined, formed, molded, extruded, etc., into desirable shapes depending on the intended uses.

Further, the porosity of such articles may be modified by any number of methods including introduction of a porogen which may be intercalated into the polymer matrix until removed by such means as solvation and sublimation, for example. The hydration of polymers may be adjusted in any manner, including removal of water by evaporation, osmosis, or any other method. Such procedures may be performed for a time, temperature, and/or pressure suitable for the intended application. Thus, in some embodiments, low temperature manufacturing processes are presented.

In some embodiments, powdered clotted blood can be used to make a bioplastic, together with water and/or glycerol plasticizer. The clotted and dried plasma may alternatively be added to virtually any plastic base material that will cure at the desired temperatures.

In some embodiments in which powdered clotted plasma is used as an ingredient in bioplastics, the powder can be adjusted to a water content of 5-15% by weight, or 8-12% by weight, or 8-10% by weight, prior to mixing the dough. By contrast, when the plasma or plasma fraction is dried through the gel phase, the water that is inherent from the original plasma clot can represent about 10-25% by weight of the starting material. Also, at any time a stabilizer may be added to the plasma to protect it during dehydration and rehydration. In some embodiments, the plasticizing temperature can be between 55-65° C. In some embodiments, the clotted dried plasma containing composition may be plasticized at temperatures up to about 150° C.

The articles of the present invention can be formed or post-fabricated to possess one or more desired mechanical properties related to a desired use. A "mechanical property" refers to essentially any property that provides some description for how a substance responds to the application of an external force. Exemplary mechanical properties include tensile strength, compression strength, flexural strength, impact strength, elongation, elasticity, stiffness, toughness, having mechanical properties similar to rubber (e.g., rubbery), etc. Tensile and compression physical properties for plastics can be determined using ASTM methods D638-03 and D695-02a, and methods referenced therein, incorporated by reference herein. Such testing can be conducted using an Instron or similar test system. Impact strength can be determined using ASTM methods D256-02a and 4508-06, and methods referenced therein, incorporated by reference herein. Flexural strength can be determined using ASTM methods D790-07 and 6272-02, and methods referenced therein, incorporated by reference herein. Toughness can be determined using ASTM method D5045-99 (2007)e1, and methods referenced therein, incorporated by reference herein.

In some embodiments, blood-derived plastic bone tissue articles are provided having a Young's Modulus ranging from about 0.03 GPa to about 50 GPa measured according to ASTM Method No. D638-03 (type V specimen, 1 mm in thickness, and conditioned for 40 hours at 23+/−2° C. and 50+/−5% humidity prior to testing at 10 mm/min test speed at a pressure of about 101 KPa (about 1 atm)) conducted using an Instron tester.

As directed in the ASTM, the Young's Modulus (elastic modulus) is defined as the ratio of stress to the corresponding strain below the proportional limit of a material, in units of force per unit area. Percent strain at failure may be obtained directly from the stress vs. strain plot used to determine the Young's Modulus. Data acquired from ASTM 638-03 can also be used to derive the stiffness of a specimen, a property which describes the resistance of an elastic body to deflection by an applied force. The stiffness is equal to the Young's Modulus multiplied by the cross-sectional area of the gagelength segment of the specimen and divided by the original grip separation distance (as defined for sample V materials tested as directed under ASTM 638-03), and is expressed in units of force per unit distance.

These articles also have a compressive strength ranging from 1 MPa to about 250 MPa according to ASTM No. D695-02a (cylindrical specimen of dimensions 12.7 mm diameter×25.4 mm length, conditioned for 40 hours at 23+/−2° C. and 50+/−5% humidity, and tested at 1.3 mm/min test speed at a pressure of about 101 KPa (about 1 atm)) using an Instron tester.

In some embodiments, blood-derived plastic tendon tissue articles are provided having a Young's Modulus ranging from about 0.5 GPa to about 1.5 GPa measured according to ASTM Method No. D-638-03 as discussed above, a percent strain at failure ranging from about 8% to about 16% according to ASTM Method No. D-638-03 measured as discussed above, and a stiffness ranging from about 100 N/mm to about 5000 N/mm according to ASTM Method No. D-638-03 measured as discussed above, the Young's Modulus, percent strain at failure and stiffness being determined at a temperature of about 25° C. and a pressure of about 101 KPa (about 1 atm).

In some embodiments, blood-derived plastic ligament tissue articles are provided having a Young's Modulus ranging from about 100 MPa to about 1000 MPa measured according to ASTM Method No. D-638-03 as discussed above, and a stiffness ranging from about 50 N/mm to about 1000 N/mm according to ASTM Method No. D-638-03 measured as discussed above, the Young's Modulus and stiffness being determined at a temperature of about 25° C. and a pressure of about 101 KPa (about 1 atm).

In some embodiments, blood-derived plastic cartilage tissue articles are provided having a Young's Modulus ranging from about 1 MPa to about 250 MPa measured according to ASTM Method No. D-638-03 as discussed above, a percent strain at failure ranging from about 0.1% to about 1% according to ASTM Method No. D-638-03 measured as discussed above, and a stiffness ranging from about 5 N/mm to about 4000 N/mm according to ASTM Method No. D-638-03 measured as discussed above, the Young's Modulus, percent strain at failure and stiffness being determined at a temperature of about 25° C. and a pressure of about 101 KPa (about 1 atm).

In some embodiments, blood-derived plastic skin tissue articles are provided comprising at least one biological response modifier, wherein the article has a Young's Modulus ranging from about 0.1 MPa to about 20 MPa measured according to the "Skin Young's Modulus Test" described below, and an elasticity ranging from about 50% to about 100% according to the Elasticity Test described below, the Young's Modulus and elasticity being determined at a temperature of about 25° C. and a pressure of about 101 KPa (about 1 atm).

In some embodiments, blood-derived plastic skin tissue articles prepared from components comprising: (1) blood plasma and (2) at least one crosslinking agent selected from the group consisting of iridoid derivatives, diimidates, diones, carbodiimides, acrylamides, sugars, proteins that are chemically different from the bioactive secretory protein, dimethylsuberimidates, aldehydes, Factor XIII, dihomo bifunctional NBS esters, carbonyldiimide, glyoxyls, proanthocyanadin, reuterin, dimethylsuberimide and mixtures thereof are provided, wherein the article has a Young's Modulus ranging from about 0.1 MPa to about 20 MPa measured according to the "Skin Young's Modulus Test" described below, and an elasticity ranging from about 50% to about 100% according to the Elasticity Test described below, the Young's Modulus and elasticity being determined at a temperature of about 25° C. and a pressure of about 101 KPa (about 1 atm).

Young's Modulus and % elasticity of thin films can be measured in a number of ways for skin, for example with suction chamber devices designed for use with skin, as described by Pedersen L., et al., "Mechanical Properties of the Skin: A Comparison Between Two Suction Cup Methods", Skin Research and Technology 9: 111-115 (2003). Briefly, in using the DermaLab system (Cortex Technology), a small suction probe is attached to the skin (or thin film) with adhesive. The probe pulls negative pressure to lift the skin a predetermined distance. The system's software uses this information to calculate Young's Modulus. Young's Modulus testing according to this method is referred to herein as the "Skin Young's Modulus Test". Elasticity is determined using data collected by the probe during both the skin elevation and retraction phases. Elasticity testing according to this method is referred to herein as the "Elasticity Test".

Other useful mechanical properties include, for example, pliability (i.e., "pliant" is the ability of a polymer to bend or deform without breaking), elasticity (i.e., "elastomeric" is the ability of a polymer to recover the original shape after deformation) and other such properties.

In some embodiments, the articles of the present invention are in the form of films. A film can be, for example, both elastic and pliant, or pliant without being elastic. Where a film is neither elastic nor pliant, it is referred to herein as "rigid". A "film" refers to a thin sheet. Thus, a film can be a sheet up to 1000 µm thickness, up to 100 µm thickness, up to 10 µm thickness, up to 1 µm thickness, or any range therebetween. A film will have many mechanical properties, such as, for example, elasticity, non-elasticity, pliancy, rigidity, etc., depending on the formulation and shape. In some embodiments, the film can have less than about 5 weight percent water content on a basis of total weight of the film, or less than about 1 weight percent water content, as desired.

In some embodiments, the articles of the present invention are in the form of powders. The term "powder" or "powdered" refers to small solid particles. Powders, as used herein, comprise particles having an average diameter of less than about 30 mesh (i.e., about 595 microns), less than about 35 mesh (i.e., about 500 microns), less than about 100 mesh (i.e., about 149 microns), less than about 200 mesh (i.e., about 74 microns), or less than about 400 mesh (i.e., about 37 microns) or about 10 to about 800 microns. A powder can be formed by any means known in the art or disclosed herein including milling, grinding, spray-drying, etc.

In some embodiments, the articles of the present invention are in the form of granules or agglomerates of powder particles. Granules can have an average diameter ranging from about 250 µm to about 5 mm. Granules can be formed, for example, by agglomerating powders or by chopping, grinding or comminuting pieces or larger sized articles. In some embodiments, the granules can be molded or extruded into various shapes, such as rods for spinal fusion.

In some embodiments, the articles of the present invention can be in the form of stacked or laminated layers of films or sheets, a tubular roll, or combinations thereof.

In some embodiments, the articles of the present invention can be in the form of a bone substitutes cartilage substitute, tendon substitute, ligament substitute, skin substitute, cornea substitute, stent, fixation plate, screw, suture or staple.

In some embodiments, the articles of the present invention can have different physical or chemical characteristics within the article, such as a gradient or multiple gradients of selected characteristics. Examples of physical characteristics that can vary within the article include density, porosity, elasticity and/or tensile strength. Examples of chemical characteristics that can vary within the article include concentration of selected biological response modifiers and/or drugs.

In some embodiments, the article can have a density gradient from a region of lower density to a region of higher density. In some embodiments, the article can have multiple regions of different gradients. In some embodiments, the article can have different regions corresponding to the tissue(s) which it is intended to replace or supplement, for example a region having physical characteristics similar to tendon and a region having physical characteristics similar to bone when the article is intended to replace or supplement tendon and bone.

In some embodiments, the article can be assembled from portions having different physical or chemical characteristics, for example by stacking layers in which one or more of the layers have different characteristics. In some embodiments, articles having different regions of porosity can be formed by assembling layers having grooves and/or perforations, filling the interstices with a porogen, then molding the assembly to evaporate the porogen and form the article. The individual layers can be formed by any suitable method, such as extrusion or molding.

In some embodiments, the articles of the present invention can be sterilized by post-treatment, for example by exposure to radiation such as gamma rays, or heating or steam sterilization in an autoclave to reduce or eliminate transmissible agents (such as fungi, bacteria, viruses, prions and spore forms, etc.), in a manner well known to those skilled in the art.

In some embodiments, the present invention provides methods of manufacturing autologous bioplastics by processing a patient's own donated blood or plasma and products produced thereby. A useful method of making such an autologous PBP is as follows. Blood can be collected at any time, such as prior to surgery. The blood can be spun down to obtain platelet-rich plasma (PRP) and/or platelet poor plasma (PPP) and/or serum, or comparable methods such as whole blood collection or via apheresis are used to collect plasma from the patient without having to collect whole blood. The blood or plasma is then clotted with calcium, thrombin or other known clotting agents to form a plasma gel. To make rubbery-to-hard plastics, the clotted blood or plasma gel can be processed into a powder by drying it (this can include first removing any retained serum or not, although it is also possible to use only serum by drying it into a powder) and then ball milling or grinding or other powdering techniques. The drying step may or may not include lyophilization, but plasma dried "through the gel phase" for use in elastomers generally should not be lyophilized if possible (see below). Alternatively, a serum-free powder can be formed by first removing serum from the gel by spinning and then drying and comminuting the remaining plasma. In general, then, the method can use blood, plasma or plasma from which one or more constituents has been removed as desired (such as serum).

Prior to further processing, the plasma powder or dried plasma gel may be treated (washed) with ethanol or propanol to sterilize it and, if desired, to remove unwanted salts from the plasma by removing the wash-step alcohol. The sterilized dried blood can be mixed with one or more of biological response modifiers, such as growth factors, drugs or other therapeutics, fillers, porogens, crosslinkers, plasticizers and stabilizers, as discussed above and then formed into a rubbery-to-hard plastic material according to methods described above and in PCT Patent Application PCT/US06/29754, (U.S. patent application Ser. No. 11/495,115). Excipients or stabilizers such as sorbitol, mannitol and/or trehalose may be added to the blood prior to processing to protect endogenous plasma proteins during lyophilization and/or subsequent milling. In some embodiments, the powder formation technique may include without limitation, jet milling, mechanical grinding/sieving, ball milling (as mentioned above) or other forms of particulate milling. In addition, putty-like graft packing materials can be made by milling the plastics into pellets and mixing the pellets with self-hardening bone cements at the time of surgery.

To make elastic sheets, the clotted plasma can be processed according to methods described in U.S. patent application Ser. No. 11/495,115. It should be noted that platelet-rich plasma has inherent antimicrobial properties, and, therefore, may not require exogenous factors to be added to produce an antimicrobial effect if such a property is desired. Alternatively, platelet-poor plasma is also useful in creating either autologous or allogeneic plastic implants or other patient biomaterials.

Fabricated plastics can be milled or otherwise shaped by various approaches including but not limited to surface texturing, cutting and grinding. Surface textures can either be machined post-fabrication or can be molded into place. Alternatively, defined nano- and micro-textures can be imparted by molds used to form plastics, allowing direct molding of surface textures during bioplastic fabrication. Such textures may facilitate cell adhesion and/or physically direct cell behavior to the PBPs.

It is possible to practice the invention in an integrated system which can be, for example, installed in a blood bank. It should be noted that although autologous or allogeneic blood can be used as a starting material for a patient's own bioplastic implant the articles of the present invention can be used to create shelf-stable implants and other materials that need not be custom manufactured patient-by-patient. In addition, the present bioplastics can be used as interfaces between tissues and prostheses to improve integration.

In some embodiments, a system is provided which comprises one or more of a centrifuge, a dryer, a powder miller, disposable molds having a variety of selected or standard shapes, compression molds and a cooperating hot press and a vacuum degasser. Custom molds, based on CT/MR imaging data, could also be made by using a compact CNC milling machine, on site, or by external vendors. Compression molds made out of disposable, high compression strength materials, for example polyetheretherketone (PEEK), can eliminate the need for cleaning and sterilizing standard molds between usages. Such a system can be placed in proximity to a blood supply source, such as a blood bank, for convenient, cost-effective and speedy preparation of plastic articles according to the present invention. Of course, the system need not be present in a blood bank or hospital.

Figure 4:
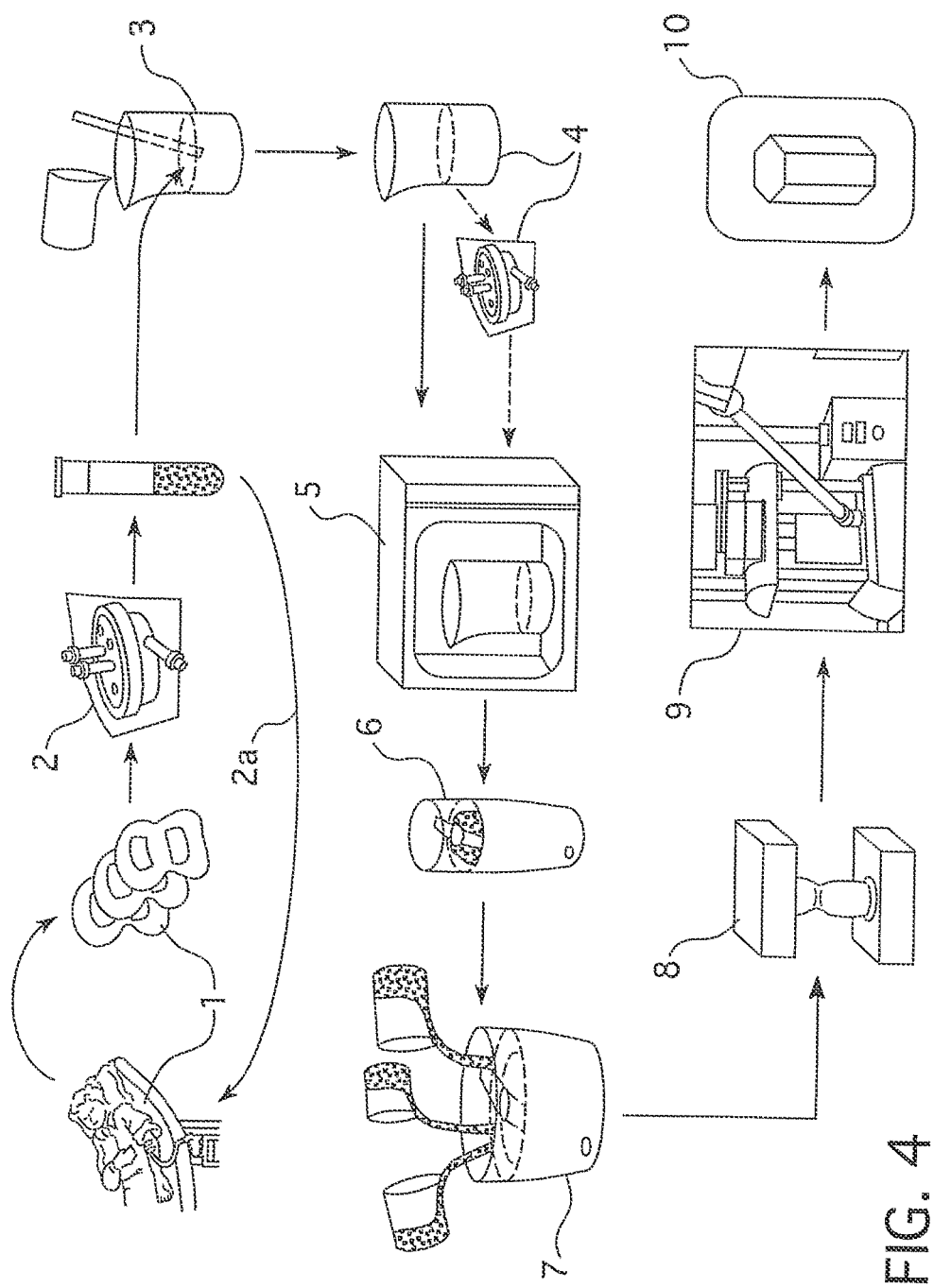
FIG. 4 is a schematic flow diagram of one embodiment of the present method for making a blood plasma-derived plastic article from blood plasma.

Referring now to FIG. 4, a schematic showing an example of the preparation of blood-derived plastic articles from clotted, dried and powdered plasma is provided. As shown in FIG. 4, a patient donates blood (1) which is spun down (2) into separated PRP or PPP plasma and red blood cells, and optionally the red blood cells are reinfused into the patient (2a). The plasma is admixed with calcium, thrombin or other clotting agent to clot the plasma (3) and to create a gel comprised of plasma clot and serum (4). The gel is dried (5) and ground into a powder or otherwise comminuted (6). The clotted dried plasma is then blended into a dough with a plasticizer, such as glycerol and/or water, together with adding any optional ingredients, such as biological response modifiers, excipients, drugs or other ingredients, and/or a thermoplastic polymer additive which supplements the bioplastic matrix (7). The composited dough is packed into a compression mold (8) and plasticized at controlled, usually low, temperature, and under pressure (9), to make an article of the present bioplastic (10). Alternatively, the same dough can be extruded instead of molded, according to means known in the art and as described above.

In some embodiments, autologous blood from a patient or subject can be harvested and processed into a powder or plastic and stored until needed. Forty-five (45) L of plasma, and possibly more, may be safely harvested by apheresis from a healthy individual every year. Taking only 25 L of plasma containing 10 grams of plasma-fibrin protein/L would yield 250 grams plasma-fibrin protein/year. Stated differently, a liter of platelet rich plasma yields 100 g solids. Considering that this yield can be mixed with various extenders, such as nanoparticulate calcium phosphate and plasticizers of various types, such as 1 part plasma to 3 parts extender(s), this would yield 1 kilogram of plastic per year per human donor. Alternatively, 100 g solids plus 66 g glycerol by weight will yield 166 g bioplastic, enough to constitute 132 cubic centimeters. The powdered plasma may be stored essentially indefinitely as a lyophilized powder or as a formed plastic under the appropriate conditions. Therefore, banking of materials becomes possible for private and/or military applications. Custom molds and compression molds, and/or extrusion, as described above, may be included.

In the event of the use of pooled plasma, precautions are taken against diseases including but not limited to blood-borne pathogens. The pooled or non-autologous products are useful in the event of a traumatic event or emergency in which the patient has no opportunity to stockpile blood or plasma in advance of a surgery or procedure. Blood banks and hospitals therefore might well find it advantageous to manufacture and store such plastics, or their immediate components, and therefore salvage at least a portion of blood that has been collected but is nearing the end of its shelf life.

Uses and applications of bioplastics formed with the articles of the present invention include, without limitation: bone grafts, including packing materials; tissue engineered scaffolds (to deliver stem cells such as embryonic, adult, autologous, allogeneic or xenogenic stem cells); fixation devices; surgical guides; scaffolds for tendon repair; prosthetic/tissue interfaces; sutures; staples; barbs; nerve guides; wound protection; and protection of dura.

In some embodiments, the articles of the present invention can be used as a permanent or resorbable coating and/or impregnant for a substrate, such as a metal substrate or polymeric substrate. Examples of suitable substrates include metal matrices, such as a mesh or stent, or a polymer or polymer-coated material such as a stent or TEFLON™ fluoropolymer coated implant. In some embodiments, a blood-derived plastic article of the present invention can comprise a coating prepared from other materials, for example polymers and/or metals such as gold or silver. Coatings can be applied in any conventional manner, such as spraying or dipping. Articles or substrates can be impregnated in any conventional manner, such as dipping or immersion. In some embodiments, a blood-derived plastic article of the present invention can be embedded within another material, for example by encasing the blood-derived plastic article within a plastic. Coatings on the surface of the blood-derived plastic article can provide a barrier to inhibit degradation of the article, for example by inhibiting cell proteolysis of the article.

In some embodiments, multiple layers of polymeric films are stacked atop one another. In such structures, gradients of bioactive materials and/or pores can be created by creating layers of the films each comprising the desired amounts of the bioactive materials within or on the surface of each layer and then stacking the different layers as desired. Such structures can be created in the manner disclosed in U.S. Pat. No. 6,165, 486, incorporated herein by reference. Such configurations can be useful when creating structures to fill cranial voids, for example.

In some embodiments, polymeric films are formed into sheets, tubes, rods, or filaments. Such structures can be useful as substitute or replacements for tendon, bone, or ligament, for example, and have application in long bone and non-long bone repair. Further incorporating growth factors or anabolic hormones and/or drugs can improve the biological response associated with tissue repair. Tube based structures also find use as tissue engineered grafts and nerve guides, for example. Also, the films can be used as barrier membranes to protect tissues and prevent tissue adhesion. The blood-plasma derived plastic articles disclosed herein offer significant advantages in promoting tissue and wound repair. Methods of forming the structure, such as tubular structures, include creating compositions which are then cast into molds. Water can then be removed from the composition (e.g., after removing the tubular structure from the mold or by using osmotic membranes as surfaces of the mold) and replaced by plasticizer. In some embodiments, sheets of the compositions disclosed herein are rolled, such as on a mandrel, to create hollow tubular structures. In some embodiments, if it is desired to have a cylindrical, non-hollow cross-section, a substantially planar composition as disclosed herein may be rolled up on itself. In some embodiments, once the cylindrical form has been attained the elastomer can be cross-linked to retain the tubular shape and/or stapled, heated to a fusing temperature, or otherwise held in the tubular configuration. In some embodiments, articles can be fused together to form composite articles having at least two portions having different physical or chemical properties.

In some embodiments, the integrity of a structure, such as those disclosed herein can be increased by including a biocompatible mesh, such as titanium, NYLO™, or DACRON™. The mesh can be added as a layer of the substantially planar material prior to rolling it into a tubular structure or it can form the outer layer of the tubular structure. In some embodiments, the materials disclosed herein can be print, cast, or extruded onto the biocompatible mesh materials. Those of skill in the art recognize that the use of mesh materials can also be used to increase the structural integrity of configurations other than tubular or cylindrical shapes.

In some embodiments, the article may be fabricated for short-term, long-term or permanent implantation into a subject. For example, a graft may be used to repair or replace diseased or damaged tissue or portions of an organ (e.g., liver, bone, heart, etc.). In some embodiments, the article can be biodegradable to form temporary structures. For example, a bone fracture may be temporarily repaired with a biodegradable article that will undergo controlled biodegradation occurring concomitantly with bioremodeling by the host's cells. In some embodiments, the article can further comprise less degradable materials to provide more permanent grafts or replacements.

In some embodiments, the methods and apparatus disclosed herein may be used to create structures with specific microstructural organization such that the structure has the anatomical and biomechanical features of naturally occurring tissues, or engineering designs that are biologically inspired.

In some embodiments, compositions comprising heat-sensitive proteins can be compressed at temperatures below the denaturation temperature or melting point of the protein, thus preserving bioactivity in the polymer matrix after compression. Pressed biopolymers may be made in any shape including 3-dimensional structures and 2-dimensional structures, such as sheets, rods, and filaments. Biopolymer structures can be prepared using different approaches (e.g., printing, casting, cold-pressing, injections molding, die extrusion etc.), wherein the amount of pressure applied controls the thickness and density of the biopolymer structure. Those of skill in the art recognize that compression may be accomplished by any means including, for example, using a pellet press. Compression may occur at any suitable combination of pressure and temperature, such as are discussed above. In some embodiments, a mold release agent, such as lecithin, is used to facilitate removal of an article from a press or mold. In some embodiments, the mold temperature is decreased from an initial value of approximately 80° C. until reaching a final steady value of approximately 25° C. (room temperature).

Those of skill in the art recognize that retention of molecules within a polymer matrix can be enhanced if the matrix is selectively permeable, i.e., the matrix allows diffusion of smaller molecules but not larger one. For example, in some embodiments, in order to prevent the passage of antibodies and other proteins having a molecular weight greater than 30,000 Daltons (Da) through the matrix but allowing passage of nutrients essential for cellular growth and metabolism, a useful permeability of the article is in the range of between 10,000 Da and 100,000 Da, for example.

The speed of erosion of a scaffold produced from a bioerodible or biodegradable polymer can be related to the molecular weights of the polymer. Higher molecular weight polymers (e.g., with average molecular weights of 90,000 Da or higher) can produce scaffolds which retain their structural integrity for longer periods of time, while lower molecular weight polymers (e.g., average molecular weights of 30,000 Da or less) can produce scaffolds which can erode much more quickly.

In some embodiments, additional features, such as roughened spots, pores, holes, etc, can be introduced into the scaffolds by machining milling, grinding, etc. to promote osteoconductive growth. Cells can readily migrate and attach upon such roughened surfaces. Introduction of pores into the compositions of the invention may also be used to regulate permeability, degradation rate, and mechanical properties of the articles disclosed herein. For example, pores may be introduced mechanically or chemically into the polymer matrix. In some embodiments, pores are introduced mechanically, such as by machining (e.g., punching) holes in a film that is subsequently stacked or rolled as described herein. In some embodiments, pores are introduced chemically by incorporating a porogen into the polymer and subsequently removing it once the polymer matrix has formed. In some embodiments, the sublimation porogen is removed by reducing pressure, such as removal using a vacuum. Vacuum pressure can be less than 100 millibars, less than 50 millibars, less than 25 millibars, less than 20 millibars, less than 15 millibars, less than 10 millibars, less than 5 millibars, less than 1 millibar, or less. In some embodiments, the sublimation porogen is removed along with water, e.g., drying a gel under a vacuum as discussed supra, and, thus, removing both water and the porogen at the drying temperatures and pressures disclosed herein. Notwithstanding the method of introduction, pores may be closed (i.e., pores not forming a contiguous space with other pores or the surface) or interconnected (i.e., pores form a contiguous space with other pores or the surface). In some embodiments, the compositions of the invention comprise interconnected pores.

Structural elastomeric and/or pliant films, grafts, and scaffolds for tissue regeneration applications are readily applicable to orthopedics, neurosurgery, and maxillofacial surgery, prosthetic tissue interface, as well as other clinical disciplines. Other useful articles that can be provided by the present invention include tissue engineered scaffolds and grafts, packing materials, fixation devices, surgical guides, prosthetic/tissue interfaces, plates, screws, sutures, staples, barbs and clips. Disclosed herein are systems, compositions, and methods useful for making and using scaffolds, which may be implanted at a desired location and can be utilized as xenografts, allografts, artificial organs, or other cellular transplantation therapeutics. These scaffolds can be used to induce a desired configuration of cell attachment/tissue formation at a specified location. The scaffold may be a permanent or long-term implant or may degrade over time as the host's natural cells replace the scaffold. The scaffold may be created in situ, or may be pre-fabricated and implanted into a patient, at a desired location using minimally invasive techniques.

In some embodiments, the blood-derived plastic articles disclosed herein may be used to create bioresorbable wound dressings or band-aids. Wound dressings may be used as a wound-healing dressing, a tissue sealant (i.e., sealing a tissue or organ to prevent exposure to a fluid or gas, such as blood, urine, air, etc., from or into a tissue or organ), and/or a cell-growth scaffold. In some embodiments, the wound dressing may protect the injured tissue, maintain a moist environment, be water permeable, easy to apply, not require frequent changes, be non-toxic, be non-antigenic, maintain microbial control, and/or deliver effective healing agents to the wound site. Wound dressings may be used in conjunction with wound repair applications, for example orthopedic applications, such as bone filling/fusion for osteoporosis and other bone diseases; cartilage repair for arthritis and other joint diseases; tendon repair; for soft tissue repair, including nerve repair, organ repair, skin repair, vascular repair, muscle repair; and ophthalmic applications. In some embodiments, wound dressings may be used in association with any medical condition that requires coating or sealing of a tissue. For example, lung tissue may be sealed against air leakage after surgery; leakage of blood, serum, urine, cerebrospinal fluid, air, mucus, tears, bowel contents, or other bodily fluids may be stopped or minimized; barriers may be applied to prevent post-surgical adhesions, including those of the pelvis and abdomen, pericardium, spinal cord and dura, tendon, and tendon sheath, treating exposed skin, in the repair or healing of incisions, abrasions, burns, inflammation, and other conditions requiring application of a coating to the outer surfaces of the body, applying coatings to other body surfaces, such as the interior or exterior of hollow organs, including blood vessels, cardiovascular surgery applications, thoracic surgery applications, neurosurgery applications, general surgery applications, repair in general trauma, plastic surgery applications, ophthalmic applications, orthopedic surgery applications, gynecology/obstetrics applications, prevention of adhesions, urology applications, dental surgery applications, and repair of incisions and other openings made for surgical purposes.

In some embodiments, the wound can be cultured to determine whether infection is present. The wound tissue can be debrided, if needed. If the culture is positive, the wound can be treated for the infection, for example by applying an antibiotic prior to or concurrently with application a blood plasma-derived plastic article of the present invention. Exemplary antibiotics include, but are not limited to, penicillin or cephalosporin. Where the culture is negative, no antibiotics need to be applied, and the wound is treated with the blood plasma-derived plastic article of the invention. For example, powder or a sheet of a blood-derived plastic article can be applied to the wound in any of a variety of formulations disclosed herein, and the wound can be dressed with conventional wound dressings, such as COMPEEL™ wound dressing, DUODERM™ wound dressing, TAGADERM™ wound dressings or OPSITE™ wound dressing. Dressings can be changed at intervals ranging between 1 day and 5 days, and may be changed at intervals of 3-4 days. Depending on the extent of damage to the underlying tissue, healing of partial thickness defect wounds can be observed in as little as 4 days and of full thickness defect wounds in as little as 2-4 weeks.

In some embodiments, the present invention provides methods for promoting healing of a skin wound comprising: applying to the skin wound surface an effective amount of a blood-derived plastic article, wherein the blood-derived plastic article comprises at least one biological response modifier. An effective amount of blood-derived plastic article can be that amount readily ascertainable by a skilled physician sufficient to promote or facilitate healing of the skin wound.

In some embodiments, the present invention provides methods for promoting healing of a tissue wound or defect comprising: applying to the tissue wound or defect an effective amount of a blood-derived plastic article, wherein the blood-derived plastic article comprises at least one biological response modifier.

In some embodiments, the present invention provides methods for providing a resorbable graft to a graft position in a subject, comprising: inserting a blood-derived plastic article into a graft position in a subject, wherein the blood-derived plastic article comprises at least one biological response modifier.

In some embodiments, the present invention provides methods for delivering stem cells to a tissue of a subject, comprising: contacting a blood-derived plastic article comprising stem cells with a tissue of a subject. The stem cells can be autologous, allogeneic, or xenogenic. The stem cells can be embryonic and/or adult. The stem cells can be seeded onto or within the blood-derived plastic article by dispersing the stem cells on top of the article or soaking the article in a composition comprising the stem cells. The article can be placed directly in contact with the tissue or cultured for a period of time to increase the concentration of stem cells therein.

In some embodiments, the present invention provides methods for connecting a first portion of a tissue with a second portion of a tissue, comprising: contacting at least one blood-derived plastic article selected from the group consisting of a suture, staple and barb with a first portion of a tissue with a second portion of a tissue such that the first portion of the tissue and the second portion of the tissue are connected. In some embodiments, the blood-derived plastic article can form bonds with the tissue to provide temporary or prolonged connection to the tissue. The tissues can be of the same or dissimilar types, for example the article can be used to connect portions of skin tissue or a portion of a bone tissue to a tendon tissue.

In some embodiments, the blood-derived plastic articles of the present invention may be used to fabricate coatings for devices to be used in the body or in contact with bodily fluids, such as medical devices, surgical instruments, diagnostic instruments, drug delivery devices, and prosthetic implants. Coatings may be fabricated directly on such objects or may be pre-fabricated in sheets, films, blocks, plugs, or other structures and applied/adhered to the device.

In some embodiments, the blood-derived plastic articles of the present invention may be placed into a seeping wound to seal off the blood flow. Such wound plug or blood clotting applications may be particularly useful, for example, in battlefield applications.

In some embodiments, the blood-derived plastic articles of the present invention may be fabricated to provide delivery of a therapeutic agent, such as a biological response modifier and/or drug, at a desired location. Therapeutic agents may be included in a coating as an ancillary to a medical treatment (for example, antibiotics) or as the primary objective of a treatment (for example, a gene to be locally delivered).

Examples of useful tissue-engineered constructs can include elastomeric sheets such as layered, rolled or tube structures and machined sheets which may include holes, possibly of defined geometries or patterns, to facilitate host tissue interstitial communication throughout the construct. Topical applications of sheet materials may include, without limitation, skin substitutes following burn and chronic non-healing wounds/sores; surgical soft tissue defect fillers; post skin and breast cancer resection; plastic surgery related applications to help minimize scarring; and dental applications, including guided tissue regeneration. Interior (rather than topical) applications include duraplasty, peripheral nerve guides, adhesion prevention in various applications such as gastrointestinal and cardiovascular surgery, hernia repair, degradable thermal insulators for cryosurgery, renal applications, anastomoses, tendon/ligament repair, heart valves and patches, bursa repair to prevent adhesions, and drug delivery of growth factors, analgesics, chemotherapeutics, antibiotics and other drugs via implanted reservoirs or impregnated plastics with or without pores.

Solid forms of the present materials (with solid ranging from rubbery plastic to very hard plastic) may be used for any of the above-mentioned applications or also in fillers or shaped grafts for craniofacial, dental, orthopaedic, neurosurgical and plastic surgical applications; or in "granular" filler, tubes and other shapes to fill defects due to trauma, cancer resection, spinal fusion, cranial defect, diseased or degraded joints such as due to arthritis or osteonecrosis; or in resorbable implants for arthroplasty, prosthetic-to-prosthetic interfaces; degradable screws, plates and other fixation devices; cartilage and meniscus graft applications; to provide fillers for cartilage defects; to create intervertebral disks to use as replacements for failed or failing disks; and to create bone resurfacing molds. Solid forms may also be used in tissue engineering applications, with capability also to deliver cells and/or growth factors for a wide range of tissue types. Such autogenic blood-derived plastic scaffolds may also be formed so as to incorporate autogenic adult stem cells. With the ever increasing potential applications of stem cells, the structures described herein could meet the demand for scaffolds capable of delivering stem cells for other than hematopoeitic stem cell applications. Microbarbs can be used for attaching graft materials, including corneal grafts, cartilage grafts, for blood vessel and other tubular structure anastomoses. Finally, for cell culture applications PBP wafers can be constructed and placed in cell culture dishes, or porous spheres can be suspended in cell culture.

Conventional bone grafts, including autografts, allografts and synthetics are far from ideal, yet these are currently the second most implanted of all biomaterials (blood products are first). Autologous and allogeneic plastics could economically address many of the problems associated with the current options. Beyond bone grafts, there are many other important applications, such as nerve guides, prosthetics/tissue interfaces, tendon repair, and wound protection bandages. A potential business model is an integrated plastics manufacturing system for hospitals that can be placed in or adjacent existing blood banks or batch manufacturing at any location, including (as recited above) a centrifuge, a dryer, a powder miller, disposable molds in standard shapes, compression molds and a cooperating hot press, and a vacuum degasser, as discussed above.

Sterilization of PBPs can be performed throughout processing, ranging from screening of plasma based on established donor collection protocols, by techniques known and developing for bacterial and viral minimization, alcohol, gamma- or other sterilization techniques of plasma powder and/or final post-packaging that represents minimal loss of biological activity, such as gamma radiation and ethylene oxide gas.

As discussed above, allogeneic grafts (such as bone grafts) have several limitations, including high variability of graft quality from donor to donor. It would be desirable to have a means to perform quality assessment (QA) and/or quality control (QC) of allogeneic graft materials with respect to the presence and/or amount of biological response modifier, such as growth factor(s), in each graft.

In some embodiments, the present invention provides methods that can be used for providing quality assessment (QA) and/or quality control (QC) of allogeneic articles, such as graft materials, with respect to the presence and/or amount of biological response modifier(s) in each article. These methods are not only applicable to assist in preparation of blood-derived plastic articles as described above, but also to any article(s) comprising biological response modifier(s) which are prepared from allogeneic blood or blood component sources.

Generally, the methods involve determining a range of acceptable concentrations of a selected biological response modifier for a batch of blood, measuring the concentration of the selected biological response modifier in each batch of blood from which an article is to be prepared, and comparing the measured concentration to determine if the measured concentration falls within the range. If the measured concentration is within the range, then the batch is acceptable for use in a composition to prepare an article. If the measured concentration is below the range, then the amount of biological response modifier in the batch can be adjusted by adding supplemental biological response modifier or mixing with batch(es) of blood having higher concentration(s) of the biological response modifier, or electing not to use the batch. If the measured concentration is above the range, then the amount of biological response modifier in the batch can be adjusted by removing excess biological response modifier or mixing with batch(es) of blood having lower concentration(s) of the biological response modifier, or electing not to use the batch. Accordingly, batches can be selected to provide desired concentration(s) of the blood modifier.

Generally, to determine the range of acceptable concentrations of the selected biological response modifier for a batch of blood, the concentration of the biological response modifier can be measured for each of a plurality of blood batches; articles can be prepared from each of the respective blood batches in a manner such as those described above; the concentration of the biological response modifier for each of the articles can be determined; a range of acceptable concentrations of the biological response modifier in an article can be determined; and the range of acceptable concentrations of the biological response modifier in the article can be correlated to a respective range of acceptable concentration of the biological response modifier in a blood batch.

Thus, in some embodiments, the present invention provides methods for assessing the concentration of a biological response modifier in an article comprising: (a) determining a range of acceptable concentrations of a pre-determined biological response modifier for a batch of blood to be used to prepare an article; (b) determining the concentration of pre-determined biological response modifier in a blood batch to be used to prepare an article; and (c) comparing the concentration determined in (b) to the range of acceptable concentrations obtained from (a). In some embodiments, the concentration of pre-determined biological response modifier can be adjusted in the blood batch that has a measured value determined in step (b) which is above or below the range determined in (a) by adding more biological response modifier and/or blood from batches having a higher or lower concentration of biological response modifier, as appropriate, to adjust the concentration accordingly. The presence and/or concentration of selected biological response modifier(s) in blood, a composition or article can be determined in a manner as discussed above, for example by corresponding assay.

In some embodiments, (a) above can be preceded by the following: (1) determining the concentration of the pre-determined biological response modifier for each of a plurality of blood batches; (2) determining the concentration of the biological response modifier for each of a plurality of blood-derived articles prepared from each of the respective blood batches of (1); (3) determining an acceptable range of concentrations of the biological response modifier for the blood-derived articles based upon the concentrations determined in (2); and (4) correlating the acceptable range of concentrations of the biological response modifier for the blood-derived plastic articles obtained from (3) with the concentrations of the biological response modifier for the blood batches obtained in (1) to determine a range of acceptable concentrations of the biological response modifier for the batch of blood of (a).

In some embodiments, the age or other physical characteristics of the donor(s) can be selected to provide blood having predetermined desired characteristics corresponding to pre-determined characteristics in the resulting articles. For example, donors of about 18 to about 30 years of age can be selected to provide blood having predetermined levels of one or more biological response modifiers.

The invention disclosed herein is exemplified by the following preparations and examples which should not be construed to limit the scope of the disclosure. Alternative mechanistic pathways and analogous structures will be apparent to those skilled in the art.

EXAMPLES

In general, initial experiments were performed using rabbit and human plasma testing such variables as dried plasma particle size, percent plasticizer (such as glycerol), plasma powder/plasticizer equilibration time, and processing temperature and pressure. Furthermore, ammonium acetate porogen and genipen crosslinking validation experiments were performed. In general, as overall conclusions, when plasma powder/plasticizer ratio is 55/45 and is held constant, and mixing equilibration time for dough mixing is varied, the resulting relative hardness of the bioplastic decreases as the dough incubation time increases. However, when plasticizer concentration is varied, while holding dough mixing and processing temperature and pressure constant, such an approach results in a decrease in relative hardness of the bioplastic as the relative plasticizer concentration increases.

Example 1

As an example of initial biocompatibility of plasma-based plastics, plasma-based constituents (plasma powder/glycerol 55/45) were vibratomed to 300 micron thickness samples and sterilized via incubation in 70% ethanol for ten minutes. Human MG-63 human osteoblastic cells were seeded upon samples and incubated for three days. Cell containing samples were processed for scanning electron microscopy (SEM). Cells exhibited ready binding, proliferation and migration upon the bioplastic surface. Furthermore, cell proteolytic remodeling of the plastic was readily apparent and extensive cellular processes are interacting directly with the bioplastic, with proteolytic degradation creating a porous material from a smooth surface.

Example 2

Rabbit plasma bioplastic samples were prepared and placed in cell free serum containing cell culture medium and held at 37° C. for up to 60 days. Samples were weighed and measured for surface area at indicated times. The bioplastic was found to swell about 50% upon addition to media but thereafter to remain constant in size throughout the duration of sampling. This indicates that the present bioplastic will not spontaneously degrade consistent with cell proteolytic degradation.

Example 3

Human plasma powder was sized into ≤38 micron and ≤150 micron distributions. Using similar processing conditions to those described in the first sentence of Example 1, processed slurries were thermomechanically molded into micron peg molds. The smaller particle size of ≤38 microns resulted in finer structural features compared to particle sizes of ≤150. In some embodiments, useful particle size ranges for the human plasma powder can be 38-500 microns, or 50-200 microns or 75-150 microns.

Example 4

Retained Biological Activity in Plasma Based Plastics (PBPs)

In some embodiments, biological activity within PBPs can be retained by appropriate processing conditions. This biological activity can be provided by growth factors and extracellular matrix (ECM) molecules contributed by platelets and to a somewhat lesser extent the plasma itself. An example of a processing parameter which can provide bioplastics with substantially preserved biological activity of biological constituents is "low" temperature processing during plastification. Such low temperature processing can be conducted at a temperature of less than about 65° C., or about 55° C. to about 65° C., or about 60° C.

As shown in Table 1, as pressing time at 60° C. increases from 7.5 to 30 minutes there was a significant loss in biological activity in the resulting PBPs. Biological activity was determined by taking known quantities of PBP samples, pulverizing to powder under liquid nitrogen, extracting soluble growth factors from the powder, and determining the ability of powder extracts to stimulate osteoblastic precursor cell proliferation in vitro.

TABLE 1

Effect of pressing time on biological activity of PBP

| Pressing Time[1] | Biological Activity (% above control)[2] |
|---|---|
| Serum Control[3] | 158[4] |
| PBP: 7.5 min | 285 |

TABLE 1-continued

Effect of pressing time on biological activity of PBP

| Pressing Time[1] | Biological Activity (% above control)[2] |
|---|---|
| PBP: 15 min | 150 |
| PBP: 30 min | 48 |

[1]PBP pressed at 60 C. at 10.7 kspi for indicated times
[2]% above non-serum, cell culture media control
[3]10% FBS in cell culture media
[4]Values represent the mean of triplicate determinations Example 5

The effect of pressure on biological activity of tested PBP samples is shown in Table 2. PBP samples subjected to the higher pressure of 14.7 kspi had similar growth factor biological activity compared to samples subjected to the lower pressure of 10.7 kspi.

TABLE 2

Effect of pressing pressure on biological activity of PBP

| Pressing Pressure[1] | Biological Activity (% above control)[2] |
|---|---|
| Serum Control[3] | 148[4] |
| PBP: 60° C., 10.7 kspi | 96 |
| PBP: 60° C., 14.7 kspi | 120 |
| PBP: 65° C., 10.7 kspi | 142 |
| PBP: 55° C., 14.7 kspi | 148 |

[1]PBP pressed at indicated temperature and pressure for 15 min
[2]% above non-serum, cell culture media control
[3]10% FBS in cell culture media
[4]Values represent the mean of triplicate determinations Example 6

Another example of retained biological activity as well as biocompatibility is depicted in FIG. 1. Osteoblastic precursor cells were cultured on PBPs and then monitored for subsequent cell interactions using scanning electron microscopy. Increasing magnification depicted in FIG. 1A-1D illustrate positive cell-PBP interaction with active remodeling of the PBP substrate.

Example 7

Genipin Modification of PBPs

Figure 2:
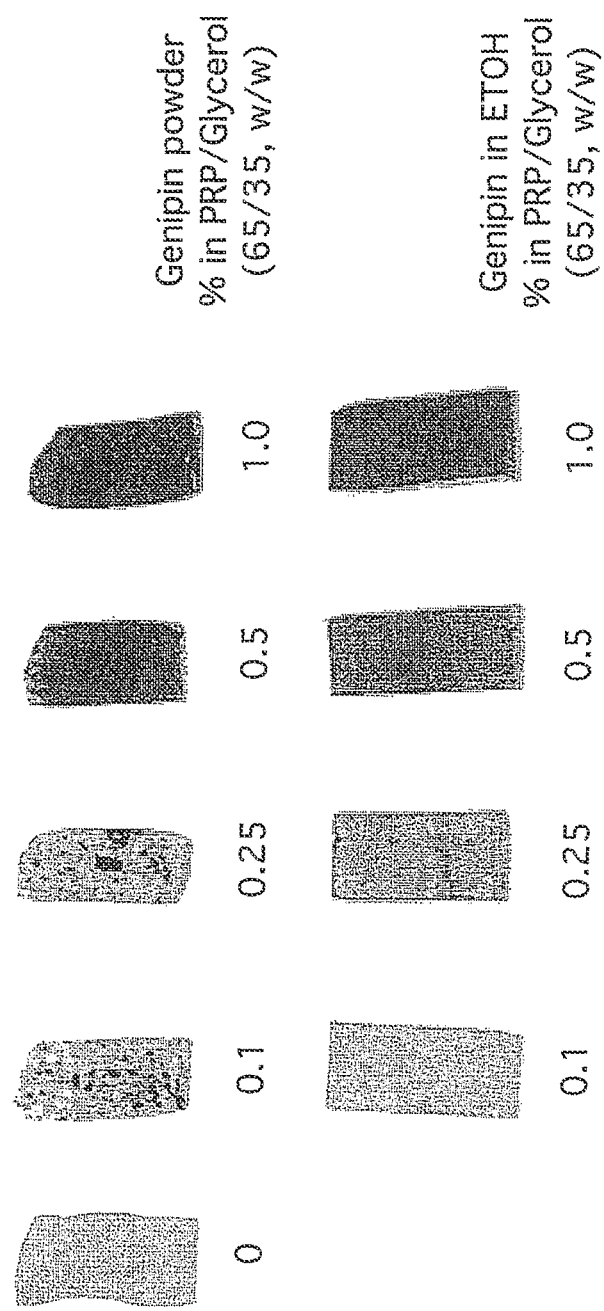
FIG. 2 depicts samples of the present blood plasma-derived plastic article in which (top row) Genipin was added as a powder to the components without prior alcohol solubilization of Genipin and (second row) Genipin solubilized in alcohol was added to the components.

As shown in this example, genipin can be added prior to plastification. Because transport of genipin is not an issue, crosslinking occurs during plastification, stabilizing the PBPs and minimizing any swelling when placed in biological fluids. FIG. 2 demonstrates that dissolving genipin crystals in ethanol prior to addition to the bioplastic dough results in a more homogeneous distribution of crosslinking (the second line of bioplastic samples is demonstrably more homogeneous than the top line). Note that when genipin is delivered in crystalline form, it first dissolves locally within the forming PBP, resulting in "islands" that eventually create a non-homogenous distribution of crosslinking in PBPs. When genipin crystals or powder are solubilized in ethanol prior to adding to the bioplastic dough phase, a homogenous color change occurs throughout the PBPs creating a more monolithic product.

Within the context of delivering growth factors and other biological components, although there is a slight loss in biological activity, substantial biological activity remains in genipin treated PBPs (Table 3). Biological assessments were conducted as with Table 1 and 2. There is no difference between the forms of genipin added to the bioplastic dough, either crystalline or dissolved in ethanol.

TABLE 3

Effect of genipin on biological activity of PBP

| PBP Sample[1] | Biological Activity (% above control)[2] |
|---|---|
| Serum Control[3] | 286 ± 22[4] |
| PBP: No Genipin | 147 ± 2.5 |
| PBP: 2% Genipin (powder) | 105 ± 4 |
| PBP: 2% Genipin (ETOH) | 102 ± 5 |
| PBP: ETOH | 127 ± 6 |

[1]PBP pressed at 60 C., 10.7 kpsi for 15 min
[2]% above non-serum, cell culture media control
[3]10% FBS in cell culture media
[4]Values represent the mean ± SEM of triplicate determinations The inclusion of genipin in PBPs can have a significant influence on PBP mechanical properties. As shown in Table 4 below, the inclusion of genipin increased the Young's modulus of tested samples by 4-9 fold.

TABLE 4

Mechanical properties of PBPs

| % Genipin | Young's Modulus (MPa) | Max Stress (MPa) |
|---|---|---|
| Powder | | |
| 0 | 9 | 1.36 |
| 1 | 50 | 1.16 |
| 2 | 80 | 2.19 |
| Powder + Water | | |
| 0 | 9 | 0.8 |
| 1 | 40 | 1.2 |
| 2 | 60 | 1.1 |
| Ethanol | | |
| 2 | 40 | 2.4 |

PBP were 65/35 PRP/glycerol (w/w) pressed at 60° C., 10.7 kpsi for 15 min

Example 8

Lyophilized Plasma Particle Size on PBP Characteristics

Figure 3:
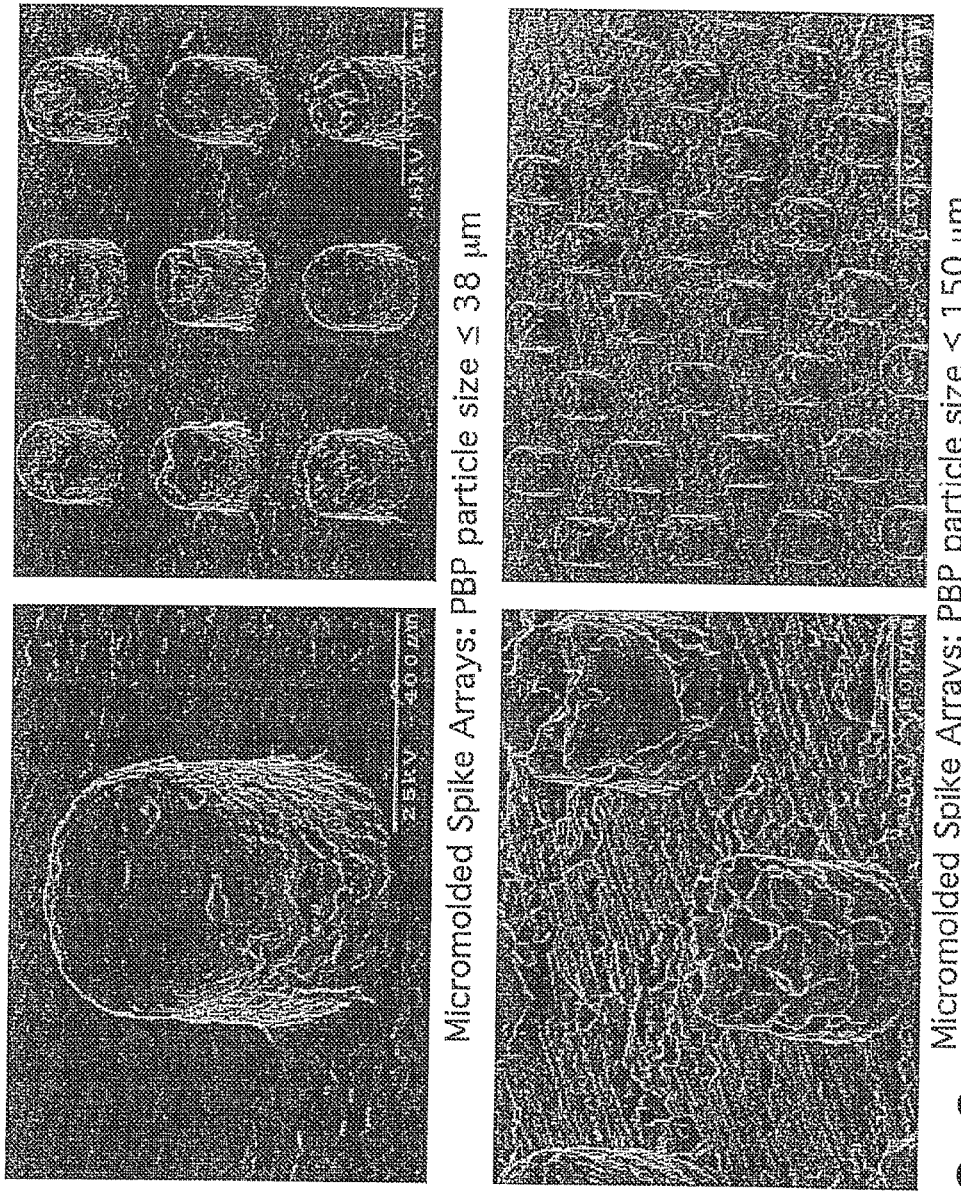
FIG. 3 depicts micrographs that illustrate how smaller particle sizes enable more and better uniformity in mold fill and molded product.

As shown in FIG. 3, smaller particle size can provide more uniform mold fill. The top row of micrograph depictions of smaller PBP particle size (≤38 μm) show more uniform mold fill than larger PBP particle size (≤150 μm). As the particle size becomes smaller this denotes a faster equilibration time of "wetting" powder with added plasticizer during the dough preparation. These properties can be desirable during micromolding or for micromachining preparation of PBP; whereas larger particle size can enable better macromolecular interlock between particles during plastification, resulting in PBPs with acceptable mechanical properties.

Example 9

Addition of Calcium Phosphate Particulates to PBPs

Calcium phosphate particulates can be added during PBP dough preparation to create PBP with both organic and inorganic components. FIG. 4 shows the addition of up to 10% nanoparticulate tricalcium phosphate (TCP) powder during dough formation with an increase in PBP opacity as TCP concentration increases. Alternatively, other clinically relevant forms of calcium phosphate, including but not limited to hydroxyapatite, can be substituted or mixed with TCP. The inclusion of such materials can alter mechanical properties, degradation, growth factor release rates, and provide additional osteoconductivity.

Example 10

Uncrosslinked PRP-PBP is Stable Under In Vitro Conditions

PRP based PBP was placed under simulated in vivo conditions, 37° C. in serum containing media for 60 days. A slight swelling occurred within the first day, but there was no subsequent change throughout the incubation period.

Example 11

Plasma Bioplastic Containing 65/35 PRP/Glycerol

Human plasma was clotted with calcium chloride by adding 1 part IM calcium chloride in water to 52.6 parts human plasma. The clot was then lyophilized (~6 mTorr) for 72 hours to a water content of 8% by weight. Plasma powder was achieved by grinding the dried material in a mechanical grinder then sieving through a 150 µm sieve. To formulate the plastic, 650 mg of plasma powder and 350 mg of glycerol were added to a small beaker. The components were mixed until homogeneous and allowed to incubate at room temperature in a closed container for approximately 21 hours. The resulting "dough" was pressed in a 13 mm diameter cylindrical press at 59° C. and 2200 lbs of pressure (10.7 kpsi) for 10 minutes. The bioplastic product (13 mm diameter×~7 mm tall) was cut into 1 mm thick slices and then seeded with human MG-63 pre-osteoblast cells. Following 4 days of growth, analysis by scanning electron microscopy (SEM) demonstrated cell proliferation and positive interaction with the plastic, as indicated by cell-mediated degradation of the bioplastic as well as multiple cellular processes interacting with the bioplastic.

Example 12

Plasma Bioplastic Containing 10% TCP and 0.5% Genipin Crosslinker 585 mg of plasma powder (described in Example 1) and 100 mg of beta-tricalcium phosphate (TCP) were added to a small beaker and thoroughly mixed with a spatula. Glycerol (315 mg) was added, followed by 73.2 µL of 68.4 mg/mL genipin dissolved in ethanol. The components were mixed until homogeneous and allowed to incubate at room temperature in a closed container for approximately 21 hours. The resulting "dough" was pressed in a 13 mm diameter cylindrical press at 59° C. and 2200 lbs of pressure (10.7 kpsi) for 10 minutes. The bioplastic product (13 mm diameter×~7 mm tall) was cut into 1 mm thick slices and then seeded with human MG-63 pre-osteoblast cells. Following one week of growth, the construct was analyzed by scanning electron microscopy (SEM) and transmission electron microscopy (TEM). Cells were shown to completely cover the bioplastic, exhibiting multiple cell layers as well as bioplastic degradation and invasion into the bioplastic.

Example 13

Plasma Bioplastic with Ammonium Acetate (50% w/w) and 0.75% Genipin 425 mg of plasma powder (described in Example 1) and 500 mg of ammonium acetate were added to a small beaker and thoroughly mixed with a spatula. Glycerol (75 mg) was added, followed by 54.9 µL of 136.7 mg/mL genipin dissolved in ethanol. The components were mixed until homogeneous and allowed to incubate at room temperature in a closed container for approximately 21 hours. The resulting "dough" was pressed in a 13 mm diameter cylindrical press at 59° C. and 2200 lbs of pressure (10.7 kpsi) for 10 minutes. The bioplastic product (13 mm diameter×~7 mm tall) was sliced into 1 mm thick slices, which were placed in a vacuum (~6 mTorr) for 48 hours to sublimate and remove the ammonium acetate. The resulting bioplastic was a porous material with 300-400 µm pore size.

Example 14

Composite Plasma Bioplastic with Differential Porosity

Plasma plastics can be made having regions comprised of different chemical or physical properties and/or materials. In this example, three doughs were prepared containing different porogen concentrations. When layered prior to compression, the final treated product contained different porosities across the sample. In dough #1, 500 mg of plasma powder (described in Example 11) was first mixed with 500 mg dextrose and then 300 mg glycerol and 100 µL of 68.4 µg/mL genipin, dissolved in ethanol. In dough #2, 750 mg of plasma powder (described in Example 11) was first mixed with 190 mg dextrose and then 280 mg glycerol and 94 µL of 68.4 µg/mL genipin dissolved in ethanol. In dough #3, 650 mg of plasma powder (described in Example 11) was mixed only with 350 mg glycerol and 73.2 µL of 68.4 µg/mL genipin dissolved in ethanol. Each respective dough was, mixed until homogeneous and allowed to incubate at room temperature in separate closed containers for approximately 21 hours. The resulting doughs were stacked (first dough on top, third dough in the middle, and second dough on the bottom) and pressed in a 13 mm diameter cylindrical press at 59° C. and 2200 lbs of pressure (10.7 kpsi) for 10 minutes. Slices of the resulting plastic were soaked in PBS (phosphate buffered saline) for two days followed by one day in ddH$_2$O (distilled deionized water), after which the samples were frozen at −20° C. and lyophilized overnight. The structure of each dried sample was then analyzed by scanning electron microscopy. The analysis showed discrete regions of porosity (boundary of dough vs. dough #3 material and dough #3 vs. dough #2 material) as well as differential porosities (dough #3 vs. dough #2 material).

It will be appreciated by those skilled in the art that changes could be made to the embodiments described above without departing from the broad inventive concept thereof. It is understood, therefore, that this invention is not limited to the particular embodiments disclosed, but it is intended to cover modifications which are within the spirit and scope of the invention, as defined by the appended claims.

What is claimed is:

1. A blood-derived plastic article comprising at least partially dried and clotted whole plasma, at least one biological response modifier, and at least one drug selected from the group consisting of an antibiotic, an analgesic, an anti-inflammatory, an immunosuppressive, an immunomodulator, and mixtures thereof.

2. The blood-derived plastic article according to claim 1, wherein the at least one drug is an antibiotic.

3. The blood-derived plastic article according to claim 2, wherein the antibiotic is a heat sensitive antibiotic.

4. The blood-derived plastic article according to claim 2, wherein the antibiotic is selected from the group consisting of cephalosporins, penicillins, sulfonamides, and tetracyclines.

5. The blood-derived plastic article according to claim 2, wherein the antibiotic is an aminoglycoside antibiotic.

6. The blood-derived plastic article according to claim 5, wherein the aminoglycoside antibiotic is selected from the group consisting of gentamicin and neomycin.

7. The blood-derived plastic article according to claim 2, wherein the antibiotic is a glycopeptide antibiotic.

8. The blood-derived plastic article according to claim 7, wherein the glycopeptide antibiotic is vancomycin.

9. The blood-derived plastic article according to claim 2, wherein the antibiotic is a macrolide antibiotic.

10. The blood-derived plastic article according to claim 9, wherein the macrolide antibiotic is selected from the group consisting of azithromycin and clarithromycin.

11. The blood-derived plastic article according to claim 2, wherein the antibiotic is a quinolone antibiotic.

12. The blood-derived plastic article according to claim 11, wherein the quinolone antibiotic is selected from the group consisting of ciprofloxacin, gatifloxacin, and levofloxacin.

13. The blood-derived plastic article according to claim 2, wherein the antibiotic is present in the blood-derived plastic article in a concentration gradient.

14. The blood-derived plastic article according to claim 1, wherein the at least one drug is a steroidal anti-inflammatory.

15. The blood-derived plastic article according to claim 1, wherein the blood-derived plastic article comprises at least two drugs, wherein at least one drug is an antibiotic and at least one drug is an analgesic.

16. The blood-derived plastic article according to claim 15, wherein the blood-derived plastic article comprises an antibiotic and an analgesic.

17. The blood-derived plastic article according to claim 15, wherein the antibiotic and the analgesic are present in the blood-derived plastic article in a concentration gradient.

18. The blood-derived plastic article according to claim 1, wherein the blood-derived plastic article comprises at least three drugs, wherein at least one drug is an antibiotic, at least one drug is an anti-inflammatory, and at least one drug is an analgesic.

19. The blood-derived plastic article according to claim 18, wherein the blood-derived plastic article comprises an antibiotic, an anti-inflammatory, and an analgesic.

20. The blood-derived plastic article according to claim 18, wherein the anti-inflammatory is present in the blood-derived plastic article in a concentration gradient.

21. The blood-derived plastic article according to claim 18, wherein the analgesic is present in the blood-derived plastic article in a concentration gradient.

22. The blood-derived plastic article according to claim 18, wherein the antibiotic, anti-inflammatory, and analgesic are present in the blood-derived article in a concentration gradient.

23. The blood-derived plastic article according to claim 1, wherein the at least one drug is lidocaine.

24. The blood-derived plastic article according to claim 1, comprising a concentration gradient of the at least one drug.

25. The blood-derived plastic article according to claim 1, wherein the at least one biological response modifier is present in the blood-derived article in a concentration gradient.

26. The blood-derived plastic article according to claim 1, wherein the at least one biological response modifier and the at least one drug are present in the blood-derived article in a concentration gradient.

27. The blood-derived plastic article according to claim 1, wherein the article is in the form of a film, patch, powder, putty, or solid block.

28. The blood-derived plastic article according to claim 1, wherein the at least one biological response modifier is a bioactive protein selected from the group consisting of hormones, growth factors, cytokines, extracellular matrix molecules, and mixtures thereof.

29. The blood-derived plastic article according to claim 28, wherein the bioactive protein comprises at least one growth factor selected from the group consisting of platelet derived growth factors (PDGF), acidic and basic fibroblast growth factors, transformation growth factor beta (TGF-beta), insulin like growth factors (IGF), epidermal growth factors (EGF), platelet-derived angiogenesis factors (PDAF), platelet-derived endothelial growth factors (PDEGF), tumor necrosis factor-alpha (TNF-α), tumor necrosis factor-beta (TNF-β), vascular endothelial growth factors (VEGF), epithelial cell growth factors (ECGF), granulocyte-colony stimulating factors (G-C SF), granulocyte-macrophage colony stimulating factors (GM-CSF), nerve growth factors (NGF), neurotrophins, erythropoietin (EPO), thrombopoietin (TPO), myostatin (GDF-8), growth differentiation factor-9 (GDF9), hepatocyte growth factors (HGF), platelet factors, and mixtures thereof.

30. The blood-derived plastic article according to claim 28, wherein the bioactive protein comprises at least one extracellular matrix molecule selected from the group consisting of osteocalcin, osteonectin, fibrinogen, vitronectin, fibronectin, thrombospondin 1 (TSP-1), bone sialoprotein (BSP), proteoglycans, and mixtures thereof.

31. The blood-derived plastic article of claim 1, wherein the platelet concentration of the whole plasma in the blood-derived plastic article is increased compared to a baseline platelet concentration of whole plasma.

32. The blood-derived plastic article according to claim 1, wherein the blood-derived plastic article further comprises at least one plasticizer.

33. The blood-derived plastic article according to claim 32, wherein the at least one plasticizer is selected from water and glycerol.

34. The blood-derived plastic article according to claim 33, wherein the at least one plasticizer is glycerol.

35. The blood-derived plastic article according to claim 32, wherein the at least one plasticizer is present in an amount of about 0.1 to about 80 percent by weight of the blood-derived plastic article.

36. The blood-derived plastic article according to claim 1, wherein the blood-derived plastic article further comprises at least one crosslinking agent.

37. The blood-derived plastic article according to claim 36, wherein the at least one crosslinking agent is genipin.

38. The blood-derived plastic article according to claim 37, wherein the at least one crosslinking agent is present in an amount of about 0.01 to about 20 percent by weight of the blood-derived plastic article.

39. A blood-derived plastic article comprising at least partially dried and clotted whole plasma, at least one biological response modifier, and at least one antibiotic.

40. The blood-derived plastic article of claim 39, wherein the at least one antibiotic is selected from the group consisting of an aminoglycoside antibiotic and a glycopeptide antibiotic.

41. The blood-derived plastic article according to claim 40, wherein the aminoglycoside antibiotic is selected from the group consisting of gentamicin and neomycin.

42. The blood-derived plastic article according to claim 40, wherein the glycopeptide antibiotic is vancomycin.

43. The blood-derived plastic article according to claim 39, wherein the at least one biological response modifier is a bioactive protein selected from the group consisting of hormones, growth factors, cytokines, extracellular matrix molecules, and mixtures thereof.

44. The blood-derived plastic article according to claim 43, wherein the bioactive protein comprises at least one growth factor selected from the group consisting of platelet derived growth factors (PDGF), acidic and basic fibroblast growth factors, transformation growth factor beta (TGF-beta), insulin like growth factors (IGF), epidermal growth factors (EGF), platelet-derived angiogenesis factors (PDAF), platelet-derived endothelial growth factors (PDEGF), tumor necrosis factor-alpha (TNF-α), tumor necrosis factor-beta (TNF-β), vascular endothelial growth factors (VEGF), epithelial cell growth factors (ECGF), granulocyte-colony stimulating factors (G-CSF), granulocyte-macrophage colony stimulating factors (GM-CSF), nerve growth factors (NGF), neurotrophins, erythropoietin (EPO), thrombopoietin (TPO), myostatin (GDF-8), growth differentiation factor-9 (GDF9), hepatocyte growth factors (HGF), platelet factors, and mixtures thereof.

45. The blood-derived plastic article according to claim 43, wherein the bioactive protein comprises at least one extracellular matrix molecule selected from the group consisting of osteocalcin, osteonectin, fibrinogen, vitronectin, fibronectin, thrombospondin 1 (TSP-1), bone sialoprotein (BSP), proteoglycans, and mixtures thereof.

46. The blood-derived plastic article of claim 39, wherein the platelet concentration of the whole plasma in the blood-derived plastic article is increased compared to a baseline platelet concentration of whole plasma.

47. The blood-derived plastic article according to claim 39, wherein the blood-derived plastic article further comprises at least one plasticizer.

48. The blood-derived plastic article according to claim 47, wherein the at least one plasticizer is selected from water and glycerol.

49. The blood-derived plastic article according to claim 48, wherein the at least one plasticizer is glycerol.

50. The blood-derived plastic article according to claim 47, wherein the at least one plasticizer is present in an amount of about 0.1 to about 80 percent by weight of the blood-derived plastic article.

51. The blood-derived plastic article according to claim 39, wherein the blood-derived plastic article further comprises at least one crosslinking agent.

52. The blood-derived plastic article according to claim 51, wherein the at least one crosslinking agent is genipin.

53. The blood-derived plastic article according to claim 51, wherein the at least one crosslinking agent is present in an amount of about 0.01 to about 20 percent by weight of the blood-derived plastic article.

* * * * *